US012654152B2

(12) United States Patent
Choi et al.

(10) Patent No.: US 12,654,152 B2
(45) Date of Patent: *Jun. 16, 2026

(54) PROCESS FOR PRODUCING A POROUS ALPHA-ALUMINA CATALYST SUPPORT

(71) Applicant: BASF SE, Ludwigshafen am Rhein (DE)

(72) Inventors: Sung Yeun Choi, Ludwigshafen am Rhein (DE); Andrey Karpov, Ludwigshafen am Rhein (DE); Christian Walsdorff, Ludwigshafen am Rhein (DE); Patrick Hubach, Ludwigshafen am Rhein (DE); Karl C. Kharas, Iselin, NJ (US)

(73) Assignee: BASF SE, Ludwigshafen am Rhein (DE)

( * ) Notice: Subject to any disclaimer, the term of this patent is extended or adjusted under 35 U.S.C. 154(b) by 492 days.

This patent is subject to a terminal disclaimer.

(21) Appl. No.: 18/011,540

(22) PCT Filed: Jun. 25, 2021

(86) PCT No.: PCT/EP2021/067499
§ 371 (c)(1),
(2) Date: Dec. 20, 2022

(87) PCT Pub. No.: WO2021/260182
PCT Pub. Date: Dec. 30, 2021

(65) Prior Publication Data
US 2023/0256414 A1 Aug. 17, 2023

(30) Foreign Application Priority Data

| Jun. 26, 2020 | (EP) | ................................ | 20182569 |
| Jun. 26, 2020 | (EP) | ................................ | 20182577 |
| Jun. 26, 2020 | (EP) | ................................ | 20182584 |

(51) Int. Cl.
*B01J 21/04* (2006.01)
*B01J 6/00* (2006.01)
(Continued)

(52) U.S. Cl.
CPC ............... *B01J 21/04* (2013.01); *B01J 6/001* (2013.01); *B01J 23/50* (2013.01); *B01J 35/40* (2024.01);
(Continued)

(58) Field of Classification Search
CPC . B01J 21/04; B01J 35/30; B01J 35/647; B01J 35/635; B01J 35/612; B01J 35/638;
(Continued)

(56) References Cited

U.S. PATENT DOCUMENTS

| 2,411,807 A | 11/1946 | Riesmeyer |
| 3,859,426 A | 1/1975 | Lambert |

(Continued)

FOREIGN PATENT DOCUMENTS

| CN | 109499558 A | 3/2019 |
| DE | 2300512 A1 | 7/1973 |

(Continued)

OTHER PUBLICATIONS

International Search Report and Written Opinion received for PCT Patent Application No. PCT/EP2021/067499, mailed on Oct. 1, 2021, 9 pages.

*Primary Examiner* — Coris Fung
*Assistant Examiner* — Catriona M Corallo
(74) *Attorney, Agent, or Firm* — Faegre Drinker Biddle & Reath LLP

(57) ABSTRACT
A process for producing a porous alpha-alumina catalyst support, comprising i) preparing a precursor material; ii) forming the precursor material into shaped bodies; and iii) calcining the shaped bodies to obtain the porous alpha-
(Continued)

alumina catalyst support. The catalyst support has a high overall pore volume, thus allowing for impregnation with a high amount of silver, while keeping its surface area sufficiently large so as to provide optimal dispersion of catalytically active species. The invention further relates to a shaped catalyst body for producing ethylene oxide by gas-phase oxidation of ethylene. Also described is a process for preparing a shaped catalyst body as described above comprising impregnating a porous alpha-alumina catalyst support obtained in the process described above with a silver impregnation solution; and b) subjecting the impregnated porous alpha-alumina support to a heat treatment.

10 Claims, 5 Drawing Sheets

(51) Int. Cl.

| | | |
|---|---|---|
| *B01J 23/50* | (2006.01) | |
| *B01J 35/40* | (2024.01) | |
| *B01J 35/61* | (2024.01) | |
| *B01J 35/63* | (2024.01) | |
| *B01J 35/64* | (2024.01) | |
| *B01J 37/02* | (2006.01) | |
| *B01J 37/08* | (2006.01) | |
| *C07C 29/50* | (2006.01) | |
| *C07D 301/10* | (2006.01) | |

(52) U.S. Cl.
CPC ........... *B01J 35/612* (2024.01); *B01J 35/635* (2024.01); *B01J 35/638* (2024.01); *B01J 35/647* (2024.01); *B01J 37/0201* (2013.01); *B01J 37/0236* (2013.01); *B01J 37/088* (2013.01); *C07C 29/50* (2013.01); *C07D 301/10* (2013.01); *B01J 2235/00* (2024.01); *B01J 2235/15* (2024.01); *B01J 2235/30* (2024.01)

(58) Field of Classification Search
CPC ... B01J 35/56; B01J 6/001; B01J 23/50; B01J 37/0201; B01J 37/0236; B01J 37/088; C07C 29/50; C07D 301/10
USPC ........................................................ 502/347
See application file for complete search history.

(56) References Cited

U.S. PATENT DOCUMENTS

| | | | | |
|---|---|---|---|---|
| 4,301,037 A | * | 11/1981 | Sanchez | ................... B01J 35/60 |
| | | | | 423/628 |
| 4,356,312 A | | 10/1982 | Nielsen et al. | |
| 4,731,350 A | | 3/1988 | Boxhoorn et al. | |
| 4,732,918 A | | 3/1988 | Lohmueller | |
| 4,908,343 A | | 3/1990 | Bhasin | |
| 4,921,681 A | | 5/1990 | Ozero et al. | |
| 5,187,140 A | | 2/1993 | Thorsteinson et al. | |
| 5,504,052 A | | 4/1996 | Rizkalla et al. | |
| 5,504,053 A | | 4/1996 | Chou et al. | |
| 5,646,087 A | | 7/1997 | Rizkalla et al. | |
| 6,165,437 A | | 12/2000 | Mohri et al. | |
| 6,452,027 B1 | | 9/2002 | Billig et al. | |
| 7,553,795 B2 | | 6/2009 | Bortinger et al. | |
| 8,378,129 B2 | | 2/2013 | Bhise et al. | |
| 8,546,297 B2 | | 10/2013 | Rokicki et al. | |
| 8,865,614 B2 | | 10/2014 | Eger et al. | |
| 2003/0191019 A1 | | 10/2003 | Rizkalla et al. | |
| 2006/0281631 A1 | | 12/2006 | Gerdes et al. | |
| 2008/0091038 A1 | | 4/2008 | Hirota et al. | |
| 2011/0077152 A1 | | 3/2011 | Gerdes et al. | |
| 2012/0065055 A1 | * | 3/2012 | Jiang | ........................ B01J 21/04 |
| | | | | 502/216 |
| 2012/0108832 A1 | | 5/2012 | Chen et al. | |
| 2014/0187417 A1 | | 7/2014 | Pak | |
| 2016/0354760 A1 | * | 12/2016 | Suchanek | ............... C04B 38/08 |
| 2021/0387958 A1 | | 12/2021 | Karpov et al. | |

FOREIGN PATENT DOCUMENTS

| | | | |
|---|---|---|---|
| DE | 2454972 | A1 | 6/1975 |
| DE | 2521906 | A1 | 12/1975 |
| DE | 3414717 | A1 | 10/1985 |
| EP | 0014457 | A2 | 8/1980 |
| EP | 0082609 | A1 | 6/1983 |
| EP | 0085237 | A1 | 8/1983 |
| EP | 0172565 | A2 | 2/1986 |
| EP | 0266015 | A1 | 5/1988 |
| EP | 0339748 | A2 | 11/1989 |
| EP | 0357293 | A1 | 3/1990 |
| EP | 0716884 | A2 | 6/1996 |
| EP | 1115486 | A1 | 7/2001 |
| EP | 1613428 | A2 | 1/2006 |
| EP | 1893331 | A1 | 3/2008 |
| EP | 1927398 | A1 | 6/2008 |
| EP | 2617489 | A1 | 7/2013 |
| EP | 3639923 | A1 | 4/2020 |
| GB | 1512625 | A | 6/1978 |
| WO | 00/09445 | A2 | 2/2000 |
| WO | 00/15334 | A1 | 3/2000 |
| WO | 01/02297 | A2 | 1/2001 |
| WO | 03/72244 | A1 | 9/2003 |
| WO | 03/72246 | A2 | 9/2003 |
| WO | 03/86624 | A1 | 10/2003 |
| WO | 2004/089537 | A2 | 10/2004 |
| WO | 2004/094055 | A2 | 11/2004 |
| WO | 2005/014482 | A2 | 2/2005 |
| WO | 2006/102189 | A1 | 9/2006 |
| WO | 2006/133183 | A2 | 12/2006 |
| WO | 2007/000664 | A1 | 1/2007 |
| WO | 2008/054564 | A1 | 5/2008 |
| WO | 2009/029419 | A1 | 3/2009 |
| WO | 2010/000720 | A2 | 1/2010 |
| WO | 2010/068332 | A1 | 6/2010 |
| WO | 2012/140614 | A1 | 10/2012 |
| WO | 2014/105770 | A1 | 7/2014 |
| WO | 2015/095508 | A1 | 6/2015 |
| WO | 2016/022709 | A1 | 2/2016 |
| WO | 2019/039930 | A1 | 2/2019 |
| WO | 2019/072597 | A1 | 4/2019 |
| WO | 2019/154863 | A1 | 8/2019 |
| WO | 2019/219892 | A1 | 11/2019 |
| WO | 2020/053563 | A1 | 3/2020 |

* cited by examiner

PROCESS FOR PRODUCING A POROUS ALPHA-ALUMINA CATALYST SUPPORT

CROSS-REFERENCE TO RELATED APPLICATIONS

This application is a National stage application (under 35 U.S.C. § 371) of PCT/EP2021/067499, filed Jun. 25, 2021, which claims benefit of European Application Nos. 20182569.2, 20182577.5, and 20182584.1, all filed Jun. 26, 2020, and all four of which are incorporated herein by reference in their entirety.

The present invention relates to a process for producing a porous alpha-alumina catalyst support, a catalyst for producing ethylene oxide by gas-phase oxidation of ethylene comprising silver deposited on a porous alumina catalyst support, a process for preparing the catalyst, and a process for producing ethylene oxide by gas-phase oxidation of ethylene.

Alumina ($Al_2O_3$) is ubiquitous in supports and/or catalysts for many heterogeneous catalytic processes. Some of these catalytic processes occur under conditions of high temperature, high pressure and/or high water-vapor pressure. It is well known that alumina has a number of crystalline phases such as alpha-alumina (often denoted as α-alumina or $\alpha$-$Al_2O_3$), gamma-alumina (often denoted as γ-alumina or $\gamma$-$Al_2O_3$) as well as a number of alumina polymorphs. alpha-Alumina is the most stable at high temperatures, but has the lowest surface area.

gamma-Alumina has a very high surface area. This is generally believed to be because the alumina molecules are in a crystalline structure that is not very densely packed. gamma-Alumina constitutes a part of the series known as activated aluminas or transition aluminas, so-called because it is one of a series of aluminas that can undergo transition to different polymorphs. Unfortunately, when gamma-alumina is heated to high temperatures, the structure of the atoms collapses such that the surface area decreases substantially. The densest crystalline form of alumina is alpha-alumina.

Ethylene oxide is produced in large volumes and is primarily used as an intermediate in the production of several industrial chemicals. In the industrial oxidation of ethylene to ethylene oxide, heterogeneous catalysts comprising silver deposited on a porous support are typically used. To carry out the heterogeneously catalyzed gas-phase oxidation, a mixture of an oxygen-comprising gas, such as air or pure oxygen, and ethylene is generally passed through a plurality of tubes which are arranged in a reactor in which a packing of shaped catalyst bodies is present.

Catalyst performance is typically characterized by selectivity, activity, longevity of catalyst selectivity and activity, and mechanical stability. Selectivity is the molar fraction of the converted olefin yielding the desired olefin oxide. Even small improvements in selectivity and the maintenance of selectivity over longer time yield huge dividends in terms of process efficiency.

For the internal surfaces of a porous supported catalyst to be utilized effectively, the feed gases must diffuse through the pores to reach the internal surfaces, and the reaction products must diffuse away from those surfaces and out of the catalyst body. In a process for producing ethylene oxide by gas-phase oxidation of ethylene, diffusion of ethylene oxide molecules out of the catalyst bodies may be accompanied by undesired consecutive reactions induced by the catalyst, such as isomerization to acetaldehyde followed by complete combustion to carbon dioxide, which reduces the overall selectivity of the process. Average molecular pore residence times and thus the extent to which undesired consecutive reactions occur are influenced by the catalyst's pore structure.

Hence, the catalytic performance is influenced by the catalyst's pore structure, which is essentially determined by the pore structure of the catalyst support. The term "pore structure" is understood to relate to the arrangement of void spaces within the support matrix, including sizes, size distribution, shapes and interconnectivity of pores. It can be characterized by various methods such as mercury porosimetry, nitrogen sorption or computer tomography. H. Giesche, "Mercury Porosimetry: A General (Practical) Overview, Part. Part. Syst. Charact. 23 (2006), 9-19, provides helpful insights with regard to mercury porosimetry.

EP 2 617 489 A1 describes a catalyst carrier wherein at least 80% of the pore volume is contained in pores with diameters in the range of from 0.1 to 10 μm, and at least 80% of the pore volume in the pores with diameters in the range of from 0.1 to 10 μm is contained in pores with diameters in the range of from 0.3 to 10 μm.

WO 03/072244 A1 and WO 03/072246 A1 each describe a catalyst carrier wherein at least 70% of the pore volume is contained in pores with diameters of from 0.2 to 10 μm and pores with diameters between 0.2 and 10 μm provide a volume of at least 0.27 mL/g of the carrier.

EP 1 927 398 A1 describes a catalyst carrier having a pore size distribution with at least two maxima in the range of 0.01 to 100 μm, with at least one of these maxima being in the range of 0.01-1.0 μm.

EP 3 639 923 A1 describes a shaped catalyst body with a multimodal pore size distribution having a maximum in the range of 0.1 to 3.0 μm and a maximum in the range of 8.0 to 100 μm, wherein at least 40% of the total pore volume of the shaped catalyst body stems from pores with a diameter in the range of 0.1 to 3.0 μm.

WO 2008/054564 A1 describes a method for producing shaped porous bodies comprising alpha-alumina platelets. US 2006/0281631 A1 describes the preparation of a carrier comprising non-platelet alumina. U.S. Pat. No. 6,165,437 A describes the preparation of alpha-alumina powders with specific morphologies by calcination of transition alumina powder in a chlorine-containing atmosphere.

There remains a significant need to enhance the performance of a supported catalyst by optimizing the alumina-based support structure and for a process for producing an optimized porous alpha-alumina catalyst support. The support structure should have a high overall pore volume, thus allowing for impregnation with a high amount of silver, while keeping its surface area sufficiently large so as to provide optimal dispersion of catalytically active species, in particular metal species. A pore structure which leads to an as high as possible rate of intra-support mass transport is also desired to minimize the average pore residence times of molecules of reactants and products and restrict the extent to which primary reaction products such as ethylene oxide undergo undesired secondary reactions during their diffusion across the pores of a supported catalyst.

The pore structure is determined by factors including size, size distribution and shape of the grains composing the matrix of the support. It has now been found that highly porous transition aluminas having a low bulk density are useful starting materials for the production of alpha-alumina catalyst supports with beneficial pore structure, in particular transition aluminas having relatively high pore volume and large pore diameters.

The invention relates to a process for producing a porous alpha-alumina catalyst support, comprising i) preparing a precursor material comprising, based on inorganic solids content, at least 50 wt.-% of a transition alumina having a loose bulk density of at most 600 g/L, a pore volume of at least 0.6 mL/g and a median pore diameter of at least 15 nm; and at most 30 wt.-% of an alumina hydrate;

ii) forming the precursor material into shaped bodies; and iii) calcining the shaped bodies to obtain the porous alpha-alumina support.

In the obtained porous alpha-alumina catalyst support, the majority of the total pore volume is contained in pores with a diameter in the range of 0.1 to 1 μm, as shown in the examples discussed below. The pores comprising the majority of the support's pore volume are thus surprisingly greater than the median pore diameter of the transition alumina by an order of magnitude.

Without wishing to be bound by theory, it is believed that pores with a diameter in the range of 0.1 to 1 μm provide a particularly suitable environment for catalytic conversion after application of a catalytic species, e.g., via impregnation. The pores are small enough to provide a large surface area, while being large enough for allowing quick diffusion of starting materials and obtained products, thus allowing for high activity and selectivity of catalysts based on such a catalyst support. Pores with a larger diameter are believed to not contribute significantly to the total surface area, thus providing less efficient reaction spaces. Pores with a diameter smaller than 0.1 μm are believed to hinder diffusion of the obtained products, which prolongs exposure of the products to the catalytic species and induces consecutive reactions, thus lowering the selectivity.

Further, the process of the invention allows for improved control of properties such as BET surface area and pore volume of the obtained alpha-alumina supports, as compared to a situation in which alpha-alumina supports are obtained via calcination of precursor materials comprising alpha-alumina. In particular, extraneous components generally understood to stabilize BET surface area and/or pore volume, such as silicon compounds, are not necessary in the process of the invention. This allows for the manufacture of alpha-alumina supports having desired BET surface area and pore volume, but having very low or zero content of impurities. Furthermore, it was found that the alpha-alumina supports of the invention exhibit sufficiently high mechanical stability.

The precursor material comprises, based on inorganic solids content, at least 50 wt.-% of a transition alumina. Preferably, the precursor material comprises, based on inorganic solids content, at least 60 wt.-%, more preferably at least 70 wt.-% of the transition alumina, such as at least 80 wt.-% or at least 90 wt.-%, in particular 95 to 100 wt.-%.

The term "transition alumina" is understood to mean an alumina comprising a metastable alumina phase, such as a gamma-, delta-, eta-, theta-, kappa- or chi-alumina phase. Preferably, the transition alumina comprises at least 80 wt.-%, preferably at least 90 wt.-%, most preferably at least 95 wt.-%, such as 95 to 100 wt.-%, of a phase selected from gamma-alumina, delta-alumina and/or theta-alumina, based on the total weight of the transition alumina, in particular a phase selected from gamma-alumina and/or delta-alumina.

The transition alumina is typically in the form of a powder. Transition aluminas are commercially available and may be obtained via thermal dehydration of hydrated aluminum compounds, in particular aluminum hydroxides and aluminum oxy-hydroxides. Suitable hydrated aluminum compounds include naturally occurring and synthetic compounds, such as aluminum trihydroxides ($Al(OH)_3$) like gibbsite, bayerite and nordstrandite, or aluminum oxy-monohydroxides (AlOOH) like boehmite, pseudoboehmite and diaspore.

By progressively dehydrating hydrated aluminum compounds, lattice rearrangements are affected. For example, boehmite can be converted to gamma-alumina at about 450° C., gamma-alumina can be converted to delta-alumina at about 750° C., and delta-alumina can be converted to theta-alumina at about 1,000° C. When heating at above 1,000° C., transition aluminas are converted to alpha-alumina.

It is believed that the morphological properties of the resulting transition aluminas are primarily dependent on the morphological properties of the hydrated aluminum compounds from which they are derived. Accordingly, Busca, "The Surface of Transitional Aluminas: A Critical Review", Catalysis Today, 226 (2014), 2-13, describes that alumina derived from a variety of pseudoboehmites have differing pore volumes and pore size distributions, despite the pseudoboehmites having similar surface areas (160~200 $m^2/g$).

In a preferred embodiment, the transition alumina comprises non-platelet crystals. The term "non-platelet" refers to any form other than platelet form, for example elongated forms such as rods or needles, or forms having approximately the same dimensions in all three spatial directions. In a preferred embodiment, the transition alumina comprises non-platelet shaped crystals, such as rod-shaped crystals as described in, e.g., WO 2010/068332 A1, or block-shaped crystals as described in, e.g., Busca, "The Surface of Transitional Aluminas: A Critical Review", Catalysis Today, 226 (2014), 2-13, see FIGS. 2c, 2d and 2e as compared to FIGS. 2a, 2b and 2f. Preferably, the average crystal size of the transition alumina is at least 5 nm, preferably at least 7 nm, most preferably at least nm, as determined via the Scherrer equation from XRD patterns.

Various synthetic methods of obtaining crystalline boehmitic alumina with high pore volume and large surface area with high thermal stability are known, e.g., from WO 00/09445 A2, WO 01/02297 A2, WO 2005/014482 A2 and WO 2016/022709 A1. For example, WO 2016/022709 A1 describes boehmitic alumina with an average pore diameter of 115 to 166 Å, a bulk density of 250 to 350 $kg/m^3$ and a pore volume of 0.8 to 1.1 $m^3/g$, prepared by precipitation of basic aluminum salts with acidic alumina salts under controlled pH and temperature. Transition aluminas produced by thermal treatment of these boehmitic aluminas and having the properties defined in the present claims are particularly suitable transition alumina for use in the process of the invention.

Prior to heat treatment, the hydrated aluminum compounds may be washed, e.g., with demineralized water, so as to reduce impurities and allow for obtaining a high purity transition alumina. For example, crystalline boehmite obtained from gibbsite by a hydrothermal process according to Chen et al., J. Solid State Chem., 265 (2018), 237 to 243, is preferably washed prior to heat treatment.

High purity transition aluminas are preferred so as to limit the content of impurities such as sodium or silicon in the catalyst support. High purity transition aluminas may be obtained, e.g., via the so-called Ziegler process, sometimes referred to as ALFOL process, and variants thereof as described in Busca, "The Surface of Transitional Aluminas: A Critical Review", in Catalysis Today, 226 (2014), 2-13.

Other processes based on the precipitation of aluminates such as sodium aluminate tend to yield transition aluminas with relatively high amounts of impurities, such as sodium.

Transition aluminas used in the present invention preferably have a total content of alkali metals, e.g., sodium and potassium, of at most 1,500 ppm, more preferably at most 600 ppm and most preferably 10 ppm to 200 ppm, relative to the total weight of the transition alumina. Various washing methods are known that allow for the reduction of the alkali metal content of the transition alumina and/or the catalyst support obtained therefrom. Washing can include washing with a base, an acid, water or other liquids.

U.S. Pat. No. 2,411,807 A describes that the sodium oxide content in alumina precipitates may be reduced by washing with a solution containing hydrofluoric acid and another acid. WO 03/086624 A1 describes carrier pretreatment with an aqueous lithium salt solution so as to remove sodium ions from the surface of a carrier. U.S. Pat. No. 3,859,426 A describes the purification of refractory oxides such as alumina and zirconia by repetitive rinsing with hot deionized water. WO 2019/039930 describes a purification method of alumina in which metal impurities were removed by extraction with an alcohol.

Besides alkali metals, the levels of other naturally occurring impurities are preferably controlled as well.

Transition aluminas used in the present invention preferably have a total content of alkaline-earth metals, such as calcium and magnesium, of at most 2,000 ppm, more preferably at most 600 ppm and most preferably at most 400 ppm, relative to the total weight of the transition alumina.

Transition aluminas used in the present invention preferably have a content of silicon of at most 10,000 ppm, preferably at most 2,000 ppm and most preferably at most 700 ppm, relative to the total weight of the transition alumina.

Transition aluminas used in the present invention preferably have a content of iron of at most 1,000 ppm, more preferably at most 600 ppm and most preferably at most 300 ppm, relative to the total weight of the transition alumina.

Transition aluminas used in the present invention preferably have a content of metals different from those mentioned above, such as titanium, zinc, zirconium, and lanthanum, of at most 1,000 ppm, more preferably at most 400 ppm and most preferably at most 100 ppm, relative to the total weight of the transition alumina.

The transition alumina has a loose bulk density of at most 600 g/L. The term "loose bulk density" is understood to be the "freely settled" or "poured" density. The "loose bulk density" thus differs from the "tapped density", where a defined mechanical tapping sequence is applied and a higher density is typically obtained. The loose bulk density may be determined by pouring the transition alumina into a graduated cylinder, suitably via a funnel, taking care not to move or vibrate the graduated cylinder. The volume and weight of the alumina are determined. The loose bulk density is determined by dividing the weight in grams by the volume in liters.

A low loose bulk density may be indicative of a high porosity and a high surface area. Preferably, the transition alumina has a loose bulk density in the range of 50 to 600 g/L, more preferably in the range of 100 to 550 g/L, most preferably 150 to 500 g/L, in particular 200 to 500 g/L or 200 to 450 g/L.

The transition alumina has a pore volume of at least 0.6 mL/g. Preferably, the transition alumina has a pore volume of 0.6 to 2.0 mL/g or 0.65 to 2.0 mL/g, more preferably 0.7 to 1.8 mL/g, most preferably 0.8 to 1.6 mL/g.

The transition alumina has a median pore diameter of at least 15 nm. The term "median pore diameter" is used herein to indicate the median pore diameter by surface area, i.e., the median pore diameter (area) is the pore diameter at the 50th percentile of the cumulative surface area graph. Preferably, the transition alumina has a median pore diameter of 15 to 500 nm, more preferably 20 to 450 nm, most preferably 20 to 300 nm, such as 20 to 200 nm.

Mercury porosimetry and nitrogen sorption are widely used to characterize the pore structure for porous materials, because these methods enable the determination of porosity and pore size distribution in one step. The two techniques are based on different physical interactions and optimally cover specific ranges of pore size.

In many cases, nitrogen sorption constitutes a sufficiently accurate determination method, particularly for smaller pores. Hence, the pore volume and the median pore diameter of transition aluminas may be determined by nitrogen sorption. Nonetheless, larger pores may be underrepresented by nitrogen sorption.

Nitrogen sorption measurements may be performed using a Micrometrics ASAP 2420. Nitrogen porosity is determined according to DIN 66134 herein, unless stated otherwise. Barrett-Joyner-Halenda (BJH) pore size and volume analysis is carried out to obtain the total pore volume ("BJH desorption cumulative pore volume") and median pore diameter ("BJH desorption average pore diameter").

Mercury porosimetry may be performed using a Micrometrics AutoPore V 9600 mercury porosimeter (140 degrees contact angle, 485 dynes/cm Hg surface tension, 61,000 psia max head pressure). For total pore volume and median pore diameter of transition aluminas, data is taken in the pore diameter range of 3 nm to 1 μm.

For adequate accuracy, the reported pore volume and the median pore diameter of transition aluminas are from nitrogen sorption if the median pore diameter from mercury porosimetry is less than 50 nm; or the reported pore volume and the median pore diameter of transition aluminas are from mercury porosimetry if the median pore diameter from mercury porosimetry is 50 nm or more.

In order to avoid falsification of the results, nitrogen sorption measurements and mercury porosimetry should be carried out on samples treated so as to remove physically adsorbed species, such as moisture, from the samples. A suitable method is described below.

The transition alumina typically has a BET surface area in the range of 20 to 500 m$^2$/g. The BET method is a standard, well-known method and widely used method in surface science for the measurements of surface areas of solids by physical adsorption of gas molecules. The BET surface is determined according to DIN ISO 9277 using nitrogen physisorption conducted at 77 K herein, unless stated otherwise. The terms "BET surface area" and "surface area" are used equivalently herein, unless noted otherwise.

The BET surface area of the transition alumina may vary over a relatively large range and may be adjusted by varying the conditions of the thermal dehydration of the hydrated aluminum compounds by which the transition alumina may be obtained. Preferably, the transition alumina has a BET surface area in the range of 20 to 200 m$^2$/g, more preferably 50 to 200 m$^2$/g or 50 to 150 m$^2$/g.

Suitable transition aluminas are commercially available. In some instances, such commercially available transition aluminas are classified as "medium porosity aluminas" or, in particular, "high porosity aluminas". Suitable transition aluminas include products of the Puralox® TH and Puralox® TM series, both from Sasol, and products of the Versal VGL series from UOP.

The transition alumina may be used in its commercially available ("unmilled") form. This commercial form of alumina comprises agglomerates (secondary particles) of the individual particles or grains (primary particles). For example, a commercial alumina particle with a mean (secondary) particle diameter (e.g., $D_{50}$) of 25 μm may comprise sub-micron sized primary particles. The mean particle diameter ($D_{50}$) as referred to herein is understood to mean the particle diameter ($D_{50}$) of secondary alumina particles.

Unmilled transition alumina powder typically has a $D_{50}$ particle diameter of 10 to 100 μm, preferably 20 to 50 μm. In addition, transition alumina may be used which has been subjected to grinding to break down the particles to a desired size. Suitably, the transition alumina may be milled in the presence of a liquid, and is preferably milled in the form of a suspension. Alternatively, grinding may be affected by dry ball-milling. Milled transition alumina powder typically has a $D_{50}$ particle diameter of 0.5 to 8 μm, preferably 1 to 5 μm. The particle size of transition alumina may be measured by laser diffraction particle size analyzers, such as a Malvern Mastersizer 2000 using water as a dispersing medium. The method includes dispersing the particles by ultrasonic treatment, thus breaking up secondary particles into primary particles. This sonication treatment is continued until no further change in the $D_{50}$ value is observed, e.g., after sonication for 3 min.

In a preferred embodiment, the transition alumina comprises at least 50 wt.-%, preferably 60 to 90 wt.-% of a transition alumina having an average particle size of 10 to 100 μm, preferably 20 to 50 μm, based on the total weight of transition alumina. Optionally, the transition alumina may comprise a transition alumina having an average particle size of 0.5 to 8 μm, preferably 1 to 5 μm, such as at most 50 wt.-%, preferably 10 to 40 wt.-%, based on the total weight of transition alumina.

The precursor material comprises, based on inorganic solids content, at most 30 wt.-% of an alumina hydrate. Preferably, the precursor material comprises, based on inorganic solids content, 1 to 30 wt.-% of the alumina hydrate, more preferably 1 to 25 wt.-%, most preferably 1 to 20 wt.-%, such as 3 to 18 wt.-%.

The term "alumina hydrate" is understood to relate to hydrated aluminum compounds as described above, in particular aluminum hydroxides and aluminum oxy-hydroxides. A discussion of the nomenclature of aluminas may be found in K. Wefers and C. Misra, "Oxides and Hydroxides of Aluminum", Alcoa Laboratories, 1987. Suitable hydrated aluminum compounds include naturally occurring and synthetic compounds, such as aluminum trihydroxides ($Al(OH)_3$) like gibbsite, bayerite and nordstrandite, or aluminum oxy-monohydroxides ($AlOOH$) like boehmite, pseudoboehmite and diaspore.

Preferably, the alumina hydrate comprises boehmite and/or pseudoboehmite. In a preferred embodiment, the total amount of boehmite and pseudoboehmite constitutes at least 80 wt.-%, more preferably at least 90 wt.-% and most preferably at least 95 wt.-%, such as 95 to 100 wt.-%, of the alumina hydrate. In an especially preferred embodiment, the amount of boehmite constitutes at least 80 wt.-%, more preferably at least 90 wt.-% and most preferably at least 95 wt.-%, such as 95 to 100 wt.-%, of the alumina hydrate.

Suitable alumina hydrates are commercially available and include products of the Pural® series from Sasol, preferably products of the Pural® TH and Pural® TM series, and products of the Versal® series from UOP.

Without wishing to be bound by theory, it is believed that the presence of alumina hydrate increases the mechanical stability of the support. In particular, it is believed that nano-sized, highly dispersible alumina hydrates suitable for colloidal applications, such as boehmites of the Disperal® or Dispal® series from Sasol exhibit high binding forces and can enhance the mechanical stability of the support especially efficiently. In general, using such nano-sized, highly dispersible alumina hydrates to improve mechanical stability may allow for relatively lower BET-surface areas at given calcination conditions.

Alumina hydrate may be partially or fully replaced by suitable alternative aluminum compounds while essentially retaining the mechanical stability of the support. Such suitable alternative aluminum compounds include aluminum alkoxides like aluminum ethoxide and aluminum isopropoxide, aluminum nitrate, aluminum acetate and aluminum acetylacetonate.

The precursor material optionally comprises a liquid. The presence, type and amount of the liquid may be chosen in accordance with the desired handling properties of the precursor material. For example, the presence of the liquid may be desirable to obtain a malleable precursor material.

The liquid is typically selected from water, in particular de-ionized water, and/or an aqueous solution comprising soluble and/or dispersible compounds selected from salts, such as ammonium acetate and ammonium carbonate; acids, such as formic acid, nitric acid, acetic acid and citric acid; bases, such as ammonia, triethylamine and methylamine; surfactants such as triethanolamine, poloxamers, fatty acid esters, and alkyl polyglucosides; submicron-sized particles, including metal oxides such as silica, titania and zirconia; clays; and/or polymer particles such as polystyrene and polyacrylates. The liquid is preferably water, most preferably de-ionized water. Typical amounts of the liquid vary in the range of from 10 to 60 wt.-%, based on the inorganic solids content of the precursor material.

The precursor material may comprise further components, which may be processing aids or which are purposively introduced to adjust the physical properties of the final catalyst support. These components include pore-forming materials, lubricants, organic binders, and/or inorganic binders.

The precursor material may comprise organic materials such as pore-forming materials, lubricants, and organic binders in a total amount of 1.0 to 60 wt.-%, preferably 3 to 50 wt.-%, based on the total weight of the precursor material.

The precursor material may comprise lubricants and organic binders in amounts 1.0 to 10 wt.-%, preferably 3 to 8 wt.-%, based on the total weight of the precursor material.

Pore-forming materials may be used to provide additional and/or wider pores in the support. The additional pore volume of wider pores can also advantageously allow for a more efficient impregnation of the support during the production of a catalyst. Preferably, pore-forming materials are essentially completely removed during heat treatment of the shaped bodies. The pore-forming function may be achieved by different mechanisms, such as combustion (i.e., burning) in the presence of oxygen, decomposition, sublimation, or volatilization.

Suitable pore-forming materials include thermally decomposable materials such as oxalic acid, malonic acid, ammonium carbonate or ammonium bicarbonate;

burnout materials, e.g., thermally combustible biomaterials such as acacia, sawdust, and flours, in particular ground nut shell flours, such as flours of pecan shells, cashew shells, walnut shells or filbert shells; and/or
organic polymers such as
    polysaccharides, such as starch, gums, cellulose and cellulose derivatives, including substituted celluloses such as methyl cellulose, ethyl cellulose, and carboxy ethyl cellulose, and cellulose ethers;
    polyolefins, like polyethylene and polypropylene;
    aromatic hydrocarbon polymers, like polystyrene;
    polycarbonates, such as poly(propylene carbonate); and
    lignins;
carbonaceous materials such as
    graphite;
    powdered carbonaceous compounds such as coke, or activated carbon powders; and
    milled or unmilled carbon fibers.

Thermally decomposable materials such as oxalic acid, malonic acid, ammonium bicarbonate or ammonium carbonate decompose upon thermal treatment and break down into volatile smaller molecules, which may or may not be combustible. For example, malonic acid decomposes upon thermal treatment to predominantly yield acetic acid and carbon dioxide. Such thermally decomposable materials may offer certain advantages in industrial processes, as these materials generally can be obtained from industrial sources with a degree of purity that they do not introduce contaminants into the support.

In order to avoid formation of a potentially explosive atmosphere, calcination of the shaped bodies is preferably conducted under an atmosphere of reduced oxygen content, such as at most 10 vol.-% or at most 5 vol.-% of oxygen, when thermally decomposable materials are used. If the thermal decomposition occurs at relatively low temperatures, the process may be safely controlled well below the ignition temperature of potentially combustible molecules formed upon decomposition of the decomposable materials. This may allow safe operation of thermal treatment even at relatively high concentrations of oxygen in the atmosphere inside the apparatus for thermal treatment. In this case, an atmosphere of air may be used.

Suitable lubricants include
    graphite;
    petroleum jelly, mineral oil, or grease;
    fatty acids, such as stearic acid or palmitic acid; salts of fatty acids, such as stearates like potassium stearate, magnesium stearate and aluminum stearate or palmitates like potassium palmitate, magnesium palmitate and aluminum palmitate; fatty acid derivatives, such as esters of fatty acids, in particular esters of saturated fatty acids, such as stearate esters like methyl and ethyl stearate; and/or
    malleable organic solids such as waxes like paraffin wax, cetyl palmitate.

It is preferable that the lubricant does not introduce inorganic contaminations into the catalyst support. Among the above-mentioned lubricants, graphite, stearic acid, aluminum stearate, and combinations thereof are preferred.

Organic binders, which sometimes are also referred to as "temporary binders" may be used to improve the malleability of the precursor material and to maintain the integrity of the "green" phase, i.e. the unfired phase, in which the mixture is formed into shaped bodies. Preferably, organic binders are essentially completely removed during heat treatment of the shaped bodies.

Suitable organic binders include
    polyvinyl lactam polymers, such as polyvinylpyrrolidones, or vinylpyrrolidone copolymers such as vinyl pyrrolidone-vinyl acetate copolymers;
    alcohols, in particular polyols such as glycol or glycerol; and/or
    polyalkylene glycols, such as polyethylene glycol.

Advantageously, pore formers and processing aids, e.g., organic binders and lubricants exhibit a low ash content. The term "ash content" is understood to relate to the incombustible component remaining after combustion of the organic materials in air at high temperature, i.e. after heat treatment of the shaped bodies. The ash content is preferably below 0.1 wt.-%, relative to the total weight of organic materials.

Moreover, pore formers and processing aids, e.g., organic binders and lubricants preferably do not form significant amounts of volatile further combustible components, such as carbon monoxide, ammonia or combustible organic compounds, upon heat treating the shaped bodies, i.e. upon thermal decomposition or combustion. An excess of volatile organic components may induce an explosive atmosphere. An appropriate safety concept is preferably applied for the combustion or decomposition process step.

Inorganic binders are permanent binders, which contribute to the adequate bonding of alumina particles and enhance the mechanical stability of the shaped alpha-alumina bodies. Inorganic binders include those which upon calcination yield exclusively aluminum oxide. For the purposes of this application, these inorganic binders are termed intrinsic inorganic binders. Such intrinsic inorganic binders include alumina hydrate as discussed above.

Extrinsic inorganic binders, on the other hand, do not exclusively yield aluminum oxide upon calcination. Suitable extrinsic inorganic binders are understood to be any of the inorganic species conventionally used in the art, e.g., silicon-containing species such as silica or silicates, including clays such as kaolinite, or metal hydroxides, metal carbonates, metal nitrates, metal acetates or metal oxides such as zirconia, titania, or alkali metal oxides. Since extrinsic inorganic binders introduce contaminants which may be detrimental to catalyst performance, they are preferably comprised in controlled amounts. Preferably, the precursor material includes extrinsic inorganic binders in amounts of 0.0 to 5.0 wt.-%, preferably 0.05 to 1.0 wt.-%, based on the inorganic solids content of the precursor material. In a preferred embodiment, the precursor material does not comprise an extrinsic inorganic binder.

The precursor material is typically obtained by dry-mixing its components, and then optionally adding the liquid. The precursor material may be formed into shaped bodies via extrusion, tableting, granulation, casting, molding, or micro-extrusion, in particular via extrusion or tableting.

The size and shape of the shaped bodies and thus of the catalyst is selected to allow a suitable packing of the catalysts obtained from the shaped bodies in a reactor tube. The catalysts obtained from the shaped bodies suitable for the catalysts of the invention are preferably used in reactor tubes with a length from 6 to 14 m and an inner diameter from 20 mm to 50 mm. In general, the support is comprised of individual bodies having a maximum extension in the range of 3 to 20 mm, such as 4 to 15 mm, in particular 5 to 12 mm. The maximum extension is understood to mean the longest straight line between two points on the outer circumference of the support.

The shape of the shaped bodies is not especially limited, and may be in any technically feasible form, depending, e.g., on the forming process. For example, the support may be a solid extrudate or a hollow extrudate, such as a hollow cylinder. In another embodiment, the support may be characterized by a multilobe structure. A multilobe structure is meant to denote a cylinder structure which has a plurality of void spaces, e.g., grooves or furrows, running in the cylinder periphery along the cylinder height. Generally, the void spaces are arranged essentially equidistantly around the circumference of the cylinder.

Preferably, the support is in the shape of a solid extrudate, such as pellets or cylinders, or a hollow extrudate, such as a hollow cylinder. In a preferred embodiment, the shaped bodies are formed by extrusion, e.g., micro-extrusion. In this case, the precursor material suitably comprises a liquid, in particular water, so as to form a malleable precursor material.

In a preferred embodiment, extrusion comprises charging at least one solid component into a mixing device before the liquid is added. Preferably, a mix-muller (H-roller) or a horizontal mixer such as a Ploughshare® mixer (from Gebrüder Lödige Maschinenbau) is used for mixing. The forming of an extrudable paste of the precursor material can be monitored and controlled based on data reflecting power consumption of the mixing device.

The precursor material is typically extruded through a die. The cross-section of the die opening is adapted according to the desired geometry of the shaped body.

The extrusion die may comprise a matrix and mandrels, wherein the matrix essentially determines the circumferential shape of the shaped bodies and the mandrels essentially determine the form, size and position of passageways, if present. Suitable extrusion dies are described in, e.g., WO 2019/219892 A1.

The geometry of the shape of the shaped bodies is defined by the geometry of the extrusion apparatus through which the precursor material is extruded. Generally, the geometry of the shape of the extrudate differs slightly from the geometry of the extrusion apparatus, while essentially having the geometric properties described above. Absolute sizes of the shape are in general slightly lower than the sizes of the extrudate, due to high temperatures required to form alpha alumina and shrinkage upon cooling of the extrudate. The extent of the shrinkage depends on the temperatures applied during calcination and the components of the shaped bodies. Therefore, the size of the extrusion dies should be routinely adjusted in a way to account for the extrudate shrinkage during the subsequent calcination.

When the shaped body comprises multiple passageways, the axes of the passageways typically run parallel. However, the shaped bodies may be slightly bent or twisted along their z axis (height). The shape of the cross-section of the passageways may be slightly different from the envisioned perfect geometrical shapes described above. When a large amount of shaped bodies is obtained, single passageways of a small number of the shaped catalyst bodies may be closed. Usually the face sides of the shaped catalyst bodies in the xy plane are more or less uneven, rather than smooth, due to the production process. The height of the shaped bodies (length of the shaped bodies in the z direction) is usually not exactly the same for all of the shaped bodies, but rather constitutes a distribution with an average height as its arithmetic mean.

The extrudate is preferably cut into the desired length while still wet. Preferably, the extrudate is cut at an angle essentially perpendicular to its circumferential surface. In order to reduce undesirable deviations from the geometry of the extrusion apparatus, the extrudate may alternatively be cut at a slanted angle of up to 30°, such as 10° or 20°, with regard to the angle perpendicular to the circumferential surface of the extrudate.

Aberrations from the geometry as incurred in the extrusion process and/or the further processing of the extrudate, e.g. a cutting step, may generally also be present in the porous alpha-alumina catalyst support of the invention obtained in the process of the invention without essentially lessening the favorable effects of its pore structure. The skilled person understands that perfect geometrical forms are fundamentally unobtainable due to the imprecision which is inherent to all production processes to some degree.

In another embodiment, the precursor material is formed into shaped bodies using a micro-extrusion process such as the one described in WO 2019/072597 A1.

In another embodiment, the precursor material is formed into shaped bodies using a gel casting process such as the one described in WO 2020/053563 A1.

In another embodiment, the precursor material is formed into shaped bodies via tableting. In this case, the precursor material typically does not comprise a liquid. Tableting is a process of press agglomeration. A powdered or previously agglomerated bulk material is introduced into a pressing tool having a die between two punches and compacted by uniaxial compression and shaped to give a solid compact. This operation is divided into four parts: metered introduction, compaction (elastic deformation), plastic deformation and ejection. Tableting is carried out, for example, on rotary presses or eccentric presses.

If desired, the upper punch and/or lower punch may comprise projecting pins to form internal passageways. It is also possible to provide the pressing punches with a plurality of movable pins, so that a punch can, for example, be made with four pins to create shaped bodies with four holes (passageways). Typical design features of such tools may be found in, e.g., U.S. Pat. No. 8,865,614 B2.

The pressing force during tableting affects compaction of the bulk material. In practice, it has been found to be useful to set the lateral compressive strength of the porous alpha-alumina catalyst support in a targeted manner by selection of the appropriate pressing force and to check this by random sampling. For the purposes of the present invention, the lateral compressive strength is the force which fractures the porous alpha-alumina catalyst support located between two flat parallel plates, with the two flat parallel end faces of the catalyst support being at right angles to the flat parallel plates.

For tableting, it is often preferable to make use of lubricants, in particular those discussed above. To improve tableting properties, a pre-granulation and/or sieving step may be used. For pre-granulation, a roll compactor, such as a Chilsonator® from Fitzpatrick, may be used. Further information regarding tableting, in particular with regard to pre-granulation, sieving, lubricants and tools, may be found in WO 2010/000720 A2.

Prior to calcining, the shaped bodies may be dried, in particular when the precursor material comprises a liquid. Suitably, drying is performed at temperatures in the range of to 400° C., in particular 30 to 300° C., such as 70 to 150° C. Drying is typically performed over a period of up to 100 h, preferably 0.5 h to 30 h, more preferably 1 h to 16 h.

Drying may be performed in any atmosphere, such as in an oxygen-containing atmosphere like air, in nitrogen, or in helium, or in mixtures thereof, preferably in air. Drying is usually carried out in an oven. The type of oven is not especially limited. For example, stationary circulating air ovens, revolving cylindrical ovens or conveyor ovens may be used. Heat may be applied directly and/or indirectly.

Preferably, flue gas (vent gas) from a combustion process having a suitable temperature is used in the drying step. The flue gas may be used in diluted or non-diluted form to provide direct heating and to remove evaporated moisture and other components liberated from the shaped bodies. The flue gas is typically passed through an oven as described above. In another preferred embodiment, off-gas from a calcination process step is used for direct heating.

Drying and calcination may be carried out sequentially in separate apparatuses and may be carried out in a batch-wise or continuous process. Intermittent cooling may be applied. In another embodiment, drying and calcination are carried out in the same apparatus. In a batch process, a time-resolved temperature ramp (program) may be applied. In a continuous process, a space-resolved temperature-ramp (program) may be applied, e.g., when the shaped bodies are continuously moved through areas (zones) of different temperatures.

Preferably, measures of heat-integration as known in the art are applied in order to improve energy efficiency. For example, relatively hotter off-gas from one process step or stage can be used to heat the feed gas, apparatus or shaped bodies in another process step or stage by direct (admixing) or indirect (heat-exchanger) means. Likewise, heat integration may also be applied to cool relatively hotter off-gas streams prior to further treatment or discharge.

The shaped bodies are calcined to obtain the porous alpha-alumina catalyst support. Thus, the calcination temperature and duration are sufficient to convert at least part of the transition alumina to alpha-alumina, meaning that at least part of the metastable alumina phases of the transition alumina is converted to alpha-alumina.

The obtained porous alpha-alumina catalyst support typically comprises a high proportion of alpha-alumina, for example at least 80 wt.-%, preferably at least 90 wt.-%, more preferably at least 95 wt.-%, most preferably at least 97.5 wt.-%, based on the total weight of the support. The amount of the alpha-alumina can for example be determined via X-ray diffraction analysis.

Typically, calcining is performed at a temperature of at least 1300° C., such as at least 1400° C., more preferably at least 1450° C. Preferably, calcining is performed at an absolute pressure in the range of 0.5 bar to 35 bar, in particular in the range of 0.9 to 1.1 bar, such as at atmospheric pressure (approximately 1013 mbar). Typical total heating times range from 0.5 to 100 h, preferably from 2 to 20 h.

Calcination is usually carried out in a furnace. The type of furnace is not especially limited. For example, furnaces such as stationary circulating air furnaces, revolving cylindrical furnaces or conveyor furnaces, or kilns such as rotary kilns or tunnel kilns, in particular roller hearth kilns, may be used.

Calcination may be performed in any atmosphere, such as in an oxygen-containing atmosphere like air, in nitrogen, or in helium, or in mixtures thereof. Preferably, in particular when the formed bodies contain a thermally decomposable material or a burnout material, calcination is at least in part or entirely carried out in an oxidizing atmosphere, such as in an oxygen-containing atmosphere like air.

As described above, pore formers and processing aids, e.g., organic binders and lubricants, preferably do not form significant amounts of volatile further combustible components, such as carbon monoxide or combustible organic compounds, upon calcining of the shaped bodies. An explosive atmosphere may further be avoided by limiting the oxygen concentration in the atmosphere during calcination, e.g., to an oxygen concentration below the limiting oxygen concentration (LOC) with respect to the further combustible components. The LOC, also known as minimum oxygen concentration (MOC), is the limiting concentration of oxygen below which combustion is not possible.

Suitably, lean air or a gaseous recycle stream with limited oxygen content may be used along with a stream for oxygen make-up, which also compensates for gaseous purge streams. In an alternative approach, an explosive atmosphere can be avoided by limiting the rate of formation of further combustible components. The rate of formation of further combustible components may be limited by heating to the calcination temperature via a slow temperature ramp, or by heating in a step-wise manner. When heating in a step-wise manner, the temperature is suitably held for several hours at the approximate combustion temperature, then heating to temperatures of 1000° C. In a continuous calcination process, the feed rate of the shaped bodies to the calcination device, e.g., the furnace, may also be controlled so as to limit the rate of formation of further combustible components.

Depending on the nature of pore-forming materials, lubricants, organic binders and gaseous components, a waste-gas treatment may be applied in order to purify any off-gas obtained during calcination. Preferably, an acidic or alkaline scrubber, a flare or catalytic combustion, a DeNOx treatment or combinations thereof may be used for off-gas treatment.

Preferably, heating takes place in a step-wise manner. In step-wise heating, the shaped bodies may be placed on a high purity and inert refractory saggar which is moved through a furnace with multiple heating zones, e.g., 2 to 8 or 2 to 5 heating zones. The inert refractory saggar may be made of alpha-alumina or corundum, in particular alpha-alumina.

The porous alpha-alumina catalyst support obtained by the process of the invention typically has a BET surface in the range of 0.5 to 5.0 m²/. Preferably, the porous alpha-alumina catalyst support has a BET surface area in the range of 0.5 to 4.5 m²/g, more preferably 1.0 to 4.5 m²/g, most preferably 1.0 to 4.0 m²/g.

The porous alpha-alumina catalyst support typically has a total pore volume of at least 0.2 mL/g, as determined by mercury porosimetry. The porous alpha-alumina catalyst support obtained by the process of the invention typically has a pore volume contained in pores with a diameter in the range of 0.1 to 1 μm of at least 40% of the total pore volume, as determined by mercury porosimetry. Preferably, the porous alpha-alumina catalyst support has a pore volume contained in pores with a diameter in the range of 0.1 to 1 μm of at least 50% of the total pore volume, more preferably at least 55% of the total pore volume, most preferably at least 60% of the total pore volume, such as at least 65% or at least 70% of the total pore volume. Typically, the porous alpha-alumina catalyst support obtained by the process of the invention has a pore volume contained in pores with a diameter in the range of 0.1 to 1 μm of preferably 40 to 99%, more preferably 45 to 99% most preferably 50 to 97% of the total pore volume.

The porous alpha-alumina catalyst support typically has a ratio $r_{pv}$ of the pore volume contained in pores with a diameter in the range of more than 1 to 10 μm to the pore volume contained in pores with a diameter in the range of 0.1 to 1 μm of at most 0.50. Preferably, the ratio of $r_{pv}$ is in the range of 0.0 to 0.45, more preferably 0.0 to 0.40 or 0.0 to 0.35.

The porous alpha-alumina support generally comprises at least 80 wt.-%, preferably at least 90 wt.-%, more preferably at least 95 wt.-%, most preferably at least 97.5 wt.-%, of alpha-alumina based on the total weight of the support.

In one embodiment, the porous alpha-alumina catalyst support comprises at least 80 wt.-% of alpha-alumina, the support having a BET surface area in the range of 0.5 to 5.0 m$^2$/g;

a total pore volume of at least 0.2 mL/g, as determined by mercury porosimetry; and a pore volume contained in pores with a diameter in the range of 0.1 to 1 µm of at least 40% of the total pore volume, as determined by mercury porosimetry;

wherein the ratio $r_{pv}$ of the pore volume contained in pores with a diameter in the range of more than 1 to 10 µm to the pore volume contained in pores with a diameter in the range of 0.1 to 1 µm is at most 0.50.

In a preferred embodiment, the porous alpha-alumina support is in the form of individual shaped bodies, e.g., in a shape as described above. Preferably, the porous alpha-alumina catalyst support is in the form of individual shaped bodies having a circumferential surface, a first side surface, a second side surface and at least one internal passageway extending from the first side surface to the second side surface.

Preferably, the quotient of the geometric surface of the catalyst support SA$_{geo}$ over the geometric volume of the catalyst support V$_{geo}$ (SA$_{geo}$/V$_{geo}$) is at least 1.1 mm$^{-1}$ and at most 10 mm$^{-1}$. Preferably, the quotient of SA$_{geo}$ over V$_{geo}$ is in the range of 1.15 mm$^{-1}$ to 5.0 mm$^{-1}$, more preferably in the range of 1.2 mm$^{-1}$ to 2.0 mm$^{-1}$. The geometric surface area SA$_{geo}$ and the geometric volume V$_{geo}$ are derived from the external, macroscopic dimensions of the porous alpha-alumina catalyst support taking into account the cross-sectional area, the height and, where applicable, the number of internal passageways. In other words, the geometric volume V$_{geo}$ of the catalyst support is the volume of a solid structure having the same outer dimensions, minus the volume occupied by passageways. Likewise, the geometric surface area SA$_{geo}$ is made up of the circumferential surface, the first and second face side surface and, where applicable, the surface defining the passageways. The first and second face side surface, respectively, is the surface area enclosed by the circumferential line of the face side, minus the cross-sectional areas of the passageways. The surface defining the passageways is the surface area lining the passageways.

A quotient of SA$_{geo}$ over V$_{geo}$ in the preferred range makes it possible for a better contact of the reaction gases with the catalyst surface to be obtained, which favors the conversion of the reactants and limits the inner diffusion phenomena, with a resulting increase in reaction selectivity.

The porous alpha-alumina support preferably does not have wash-coat particles or a wash-coat layer on its surface, so as to fully maintain the porosity of the uncoated support.

The porous alpha-alumina catalyst support may comprise impurities, such as sodium, potassium, magnesium, calcium, silicon, iron, titanium and/or zirconium. Such impurities may be introduced by components of the precursor material, in particular inorganic binders or mechanical stability enhancers. In one embodiment, the porous alpha-alumina catalyst support comprises a total amount of up to 1,500 ppmw of sodium and potassium;

up to 2,000 ppmw of calcium;

up to 1,000 ppmw of magnesium;

up to 10,000 ppmw of silicon;

up to 1,000 ppmw of titanium;

up to 1,000 ppmw of iron; and/or up to 10,000 ppmw of zirconium;

relative to the total weight of the support.

A low content of sodium is preferred in order to prevent segregation of the supported metal and to prevent alteration of the supported component.

The invention further relates to a shaped catalyst body for producing ethylene oxide by selective gas-phase oxidation (epoxidation) of ethylene, i.e. an epoxidation catalyst, comprising at least 15 wt.-% of silver, relative to the total weight of the shaped catalyst body, deposited on a porous alpha-alumina catalyst support as described above.

The shaped catalyst body typically comprises 15 to 70 wt.-% of silver, preferably 20 to 60 wt.-% of silver, more preferably 25 to 50 wt.-% or 30 to 50 wt.-% of silver, relative to the total weight of the shaped catalyst body. A silver content in this range allows for a favorable balance between turnover induced by each shaped catalyst body and cost-efficiency of preparing the shaped catalyst body.

Besides silver, the shaped catalyst body may comprise one or more promoting species. A promoting species denotes a component that provides an improvement in one or more of the catalytic properties of the catalyst when compared to a catalyst not containing said component. The promoting species can be any of those species known in the art that function to improve the catalytic properties of the silver catalyst. Examples of catalytic properties include operability (resistance to runaway), selectivity, activity, turnover and catalyst longevity.

The shaped catalyst body may comprise a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof. In one embodiment, the transition metal promoter(s) is (are) present in a total amount from 150 ppm to 5,000 ppm, typically 225 ppm to 4,000 ppm, most typically from 300 ppm to 3,000 ppm, expressed in terms of metal(s) relative to the total weight of the shaped catalyst body.

Of the transition metal promoters listed, rhenium (Re) is a particularly efficacious promoter for ethylene epoxidation high selectivity catalysts. The rhenium component in the shaped catalyst body can be in any suitable form, but is more typically one or more rhenium-containing compounds (e.g., a rhenium oxide) or complexes.

In some embodiments, the shaped catalyst body may include a promoting amount of an alkali metal or a mixture of two or more alkali metals. Suitable alkali metal promoters include, for example, lithium, sodium, potassium, rubidium, cesium or combinations thereof. The amount of alkali metal, e.g. potassium, will typically range from 50 ppm to 5,000 ppm, more typically from 300 ppm to 2,500 ppm, most typically from 500 ppm to 1,500 ppm expressed in terms of the alkali metal relative to the total weight of the shaped catalyst body. The amount of alkali metal is determined by the amount of alkali metal contributed by the porous alpha-alumina catalyst support and the amount of alkali metal contributed by the impregnation solution described below.

Combinations of heavy alkali metals like cesium (Cs) or rubidium (Rb) with light alkali metals like lithium (Li), sodium (Na) and potassium (K) are particularly preferred.

The shaped catalyst body may also include a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The shaped catalyst body may also include a promoting amount of a main group element or a mixture of two or more main group elements. Suitable main group elements include any of the elements in Groups IIIA (boron group) to VIIA (halogen group) of the Periodic Table of the Elements. For example, the shaped catalyst body can include a promoting amount of sulfur, phosphorus, boron, halogen (e.g., fluorine), gallium, or a combination thereof.

The shaped catalyst body may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

The invention further relates to a process for preparing a shaped catalyst body as described above, comprising a) impregnating a porous alpha-alumina catalyst support as described above with a silver impregnation solution, preferably under reduced pressure; and optionally subjecting the impregnated porous alumina support to drying; and b) subjecting the impregnated porous alpha-alumina support to a heat treatment;

wherein steps a) and b) are optionally repeated.

It is understood that all embodiments of the shaped catalyst body also apply to the process for preparing the shaped catalyst body, where applicable.

In order to obtain a shaped catalyst body having high silver contents, steps i) and ii) can be repeated several times. In that case it is understood that the intermediate product obtained after the first (or subsequent up to the last but one) impregnation/calcination cycle comprises a part of the total amount of target Ag and/or promoter concentrations. The intermediate product is then again impregnated with the silver impregnation solution and calcined to yield the target Ag and/or promoter concentrations.

Any silver impregnation solution suitable for impregnating a refractory support known in the art can be used. Silver impregnation solutions typically contain a silver carboxylate, such as silver oxalate, or a combination of a silver carboxylate and oxalic acid, in the presence of an aminic complexing agent like a $C_1$-$C_{10}$-alkylenediamine, in particular ethylenediamine. Suitable impregnation solutions are described in EP 0 716 884 A2, EP 1 115 486 A1, EP 1 613 428 A1, U.S. Pat. No. 4,731,350 A, WO 2004/094055 A2, WO 2009/029419 A1, WO 2015/095508 A1, U.S. Pat. Nos. 4,356,312 A, 5,187,140 A, 4,908,343 A, 5,504,053 A and WO 2014/105770 A1. For a discussion of suitable silver impregnation solutions, see also Kunz, C. et al., On the Nature of Crystals Precipitating from Aqueous Silver Ethylenediamine Oxalate Complex Solutions., Z. Anorg. Allg. Chem., 2021, 647, DOI: 10.1002/zaac.202100079.

During heat treatment, liquid components of the silver impregnation solution evaporate, causing a silver compound comprising silver ions to precipitate from the solution and be deposited onto the porous support. At least part of the deposited silver ions is subsequently converted to metallic silver upon further heating. Preferably, at least 70 mol-% of the silver compounds, preferably at least 90 mol-%, more preferably at least 95 mol-% and most preferably at least 99.5 mol-% or at least 99.9 mol-%, i.e. essentially all of the silver ions, based on the total molar amount of silver in the impregnated porous alpha-alumina support, respectively. The amount of the silver ions converted to metallic silver can for example be determined via X-ray diffraction (XRD) patterns.

The heat treatment may also be referred to as a calcination process. Any calcination processes known in the art for this purpose can be used. Suitable examples of calcination processes are described in U.S. Pat. Nos. 5,504,052 A, 5,646,087 A, 7,553,795 A, 8,378,129 A, 8,546,297 A, US 2014/0187417 A1, EP 1 893 331 A1 or WO 2012/140614 A1. Heat treatment can be carried out in a pass-through mode or with at least partial recycling of the calcination gas.

Heat treatment is usually carried out in a furnace. The type of furnace is not especially limited. For example, stationary circulating air furnaces, revolving cylindrical furnaces or conveyor furnaces may be used. In one embodiment, heat treatment constitutes directing a heated gas stream over the impregnated bodies. The duration of the heat treatment is generally in the range of 5 min to 20 h, preferably 5 min to 30 min.

The temperature of the heat treatment is generally in the range of 200 to 800° C., preferably 210 to 650° C., more preferably 220 to 500° C., most preferably 220 to 350° C. Preferably, the heating rate in the temperature range of 40 to 200° C. is at least 20 K/min, more preferably at least 25 K/min, such as at least 30 K/min. A high heating rate may be achieved by directing a heated gas over the impregnated refractory support or the impregnated intermediate catalyst at a high gas flow.

A suitable flow rate for the gas may be in the range of, e.g., 1 to 1,000 Nm³/h, 10 to 1,000 Nm³/h, 15 to 500 Nm³/h or 20 to 300 Nm³/h per kg of impregnated bodies. In a continuous process, the term "kg of impregnated bodies" is understood to mean the amount of impregnated bodies (in kg/h) multiplied by the time (in hours) that the gas stream is directed over the impregnated bodies. It has been found that when the gas stream is directed over higher amounts of impregnated bodies, e.g., 15 to 150 kg of impregnated bodies, the flow rate may be chosen in the lower part of the above-described ranges, while achieving the desired effect.

Determining the temperature of the heated impregnated bodies directly may pose practical difficulties. Hence, when a heated gas is directed over the impregnated bodies during heat treatment, the temperature of the heated impregnated bodies is considered to be the temperature of the gas immediately after the gas has passed over the impregnated bodies. In a practical embodiment, the impregnated bodies are placed on a suitable surface, such as a wire mesh or perforated calcination belt, and the temperature of the gas is measured by one or more thermocouples positioned adjacent to the opposite side of the impregnated bodies which first comes into contact with the gas. The thermocouples are suitably placed close to the impregnated bodies, e.g., at a distance of 1 to 30 mm, such as 1 to 3 mm or 15 to 20 mm from the impregnated bodies.

The use of a plurality of thermocouples can improve the accuracy of the temperature measurement. Where several thermocouples are used, these may be evenly spaced across the area on which the impregnated bodies rest on the wire mesh, or the breadth of the perforated calcination belt. The average value is considered to be the temperature of the gas immediately after the gas has passed over the impregnated bodies. To heat the impregnated bodies to the temperatures as described above, the gas typically has a temperature of 220 to 800° C., more preferably 230 to 550° C., most preferably 240 to 350° C.

Preferably, heating takes place in a step-wise manner. In step-wise heating, the impregnated bodies are placed on a moving belt that moves through a furnace with multiple heating zones, e.g., 2 to 8 or 2 to 5 heating zones. Heat treatment is preferably performed in an inert atmosphere, such as nitrogen, helium, or mixtures thereof, in particular in nitrogen.

The invention further relates to a process for producing ethylene oxide by selective gas-phase oxidation (epoxidation) of ethylene, comprising reacting ethylene and oxygen in the presence of a shaped catalyst body as described above.

It is understood that all embodiments of the shaped catalyst body also apply to the process for producing ethylene oxide in the presence of the shaped catalyst body, where applicable.

The epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE 34 14 717 A1, EP 0 082 609 A1 and EP 0 339 748 A2.

The epoxidation is preferably carried out in at least one tube reactor, preferably in a shell-and-tube reactor. On a commercial scale, ethylene epoxidation is preferably carried out in a multi-tube reactor that contains several thousand tubes. The catalyst is filled into the tubes, which are placed in a shell that is filled with a coolant. In commercial applications, the internal tube diameter is typically in the range of 20 to 40 mm (see, e.g., U.S. Pat. No. 4,921,681 A) or more than 40 mm (see, e.g., WO 2006/102189 A1).

To prepare ethylene oxide from ethylene and oxygen, it is possible to carry out the reaction under conventional reaction conditions as described, for example, in DE 25 21 906 A, EP 0 014 457 A2, DE 23 00 512 A1, EP 0 172 565 A2, DE 24 54 972 A1, EP 0 357 293 A1, EP 0 266 015 A1, EP 0 085 237 A1, EP 0 082 609 A1 and EP 0 339 748 A2. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen.

The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas.

The reaction gas preferably comprises a chlorine-comprising reaction moderator such as ethyl chloride, vinyl chloride or 1,2-dichloroethane in an amount of from 0 to 15 ppm by weight, preferably in an amount of from 0.1 to 8 ppm by weight, based on the total weight of the reaction gas. The remainder of the reaction gas generally comprises hydrocarbons such as methane and also inert gases such as nitrogen. In addition, other materials such as steam, carbon dioxide or noble gases can also be comprised in the reaction gas.

The concentration of carbon dioxide in the feed (i.e. the gas mixture fed to the reactor) typically depends on the catalyst selectivity and the efficiency of the carbon dioxide removal equipment. Carbon dioxide concentration in the feed is preferably at most 3 vol.-%, more preferably less than 2 vol.-%, most preferably less than 1 vol.-%, relative to the total volume of the feed. An example of carbon dioxide removal equipment is provided in U.S. Pat. No. 6,452,027 B1.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene, which typically has a purity of at least 99%, and "chemical-grade" ethylene which typically has a purity of less than 95%. The impurities typically comprise, in particular, ethane, propane and/or propene.

The reaction or oxidation of ethylene to ethylene oxide is usually carried out at elevated catalyst temperatures. Preference is given to catalyst temperatures in the range of 150 to 350° C., more preferably 180 to 300° C., particularly preferably 190 to 280° C. and especially preferably 200 to 280° C. The present invention therefore also provides a process as described above in which the oxidation is carried out at a catalyst temperature in the range 180 to 300° C., preferably 200 to 280° C. Catalyst temperature can be determined by thermocouples located inside the catalyst bed. As used herein, the catalyst temperature or the temperature of the catalyst bed is deemed to be the weight average temperature of the catalyst particles.

The reaction according to the invention (oxidation) is preferably carried out at pressures in the range of 5 to 30 bar. All pressures herein are absolute pressures, unless noted otherwise. The oxidation is more preferably carried out at a pressure in the range of 5 to bar, such as 10 bar to 24 bar and in particular 14 bar to 23 bar. The present invention therefore also provides a process as described above in which the oxidation is carried out at a pressure in the range of 14 bar to 23 bar.

It has been found that the physical characteristics of the shaped catalyst body, especially the BET surface area and the pore size distribution have a significant positive impact on the catalyst selectivity. This effect is especially distinguished when the catalyst is operated at very high work rates, i.e., high levels of olefin oxide production.

The process according to the invention is preferably carried out under conditions conducive to obtain a reaction mixture containing at least 2.3 vol.-% of ethylene oxide. In other words, the ethylene oxide outlet concentration (ethylene oxide concentration at the reactor outlet) is preferably at least 2.3 vol.-%. The ethylene oxide outlet concentration is more preferably in the range of 2.5 to 4.0 vol.-%, most preferably in the range of 2.7 to 3.5 vol.-%.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10,000/h, preferably in the range from 2,000 to 8,000/h, more preferably in the range from 2,500 to 6,000/h, most preferably in the range from 4,500 to 5,500/h, where the values indicated are based on the volume of the catalyst.

According to a further embodiment, the present invention is also directed to a process for preparing ethylene oxide (EO) by gas-phase oxidation of ethylene by means of oxygen as disclosed above, wherein the EO-space-time-yield measured is greater than 180 $kg_{EO}/(m^3_{cat}h)$, preferably to an EO-space-time-yield of greater than 200 $kg_{EO}/(m^3_{cat}h)$, such as greater than 250 $kg_{EO}/(m^3_{cat}h)$, greater than 280 $kg_{EO}/(m^3_{cat}h)$, or greater than 300 $kg_{EO}/(m^3_{cat}h)$. Preferably the EO-space-time-yield measured is less than 500 $kg_{EO}/(m^3_{cat}h)$, more preferably the EO-space-time-yield is less than 350 $kg_{EO}/(m^3_{cat}h)$.

The preparation of ethylene oxide from ethylene and oxygen can advantageously be carried out in a recycle process. After each pass, the newly formed ethylene oxide and the by-products formed in the reaction are removed from the product gas stream. The remaining gas stream is supplemented with the required amounts of ethylene, oxygen and reaction moderators and reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The invention is described in more detail by the accompanying drawings and the subsequent examples.

Method 1: Nitrogen Sorption

Figure 1:
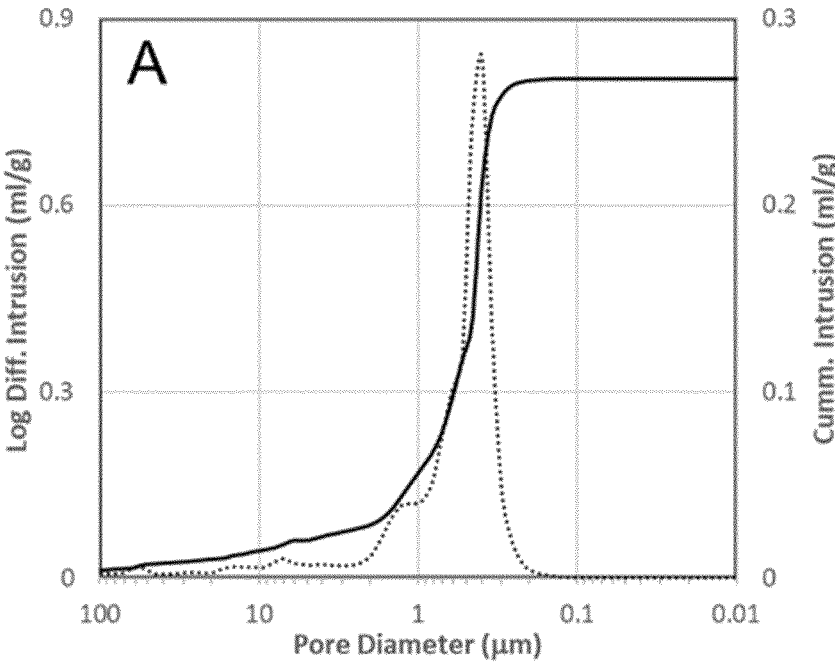
FIG. 1 shows the log differential intrusion [mL/g] and cumulative intrusion [mL/g] relative to the pore size diameter [mL/g] of inventive porous alpha-alumina catalyst support A, obtained by a process according to the invention.
Figure 2:
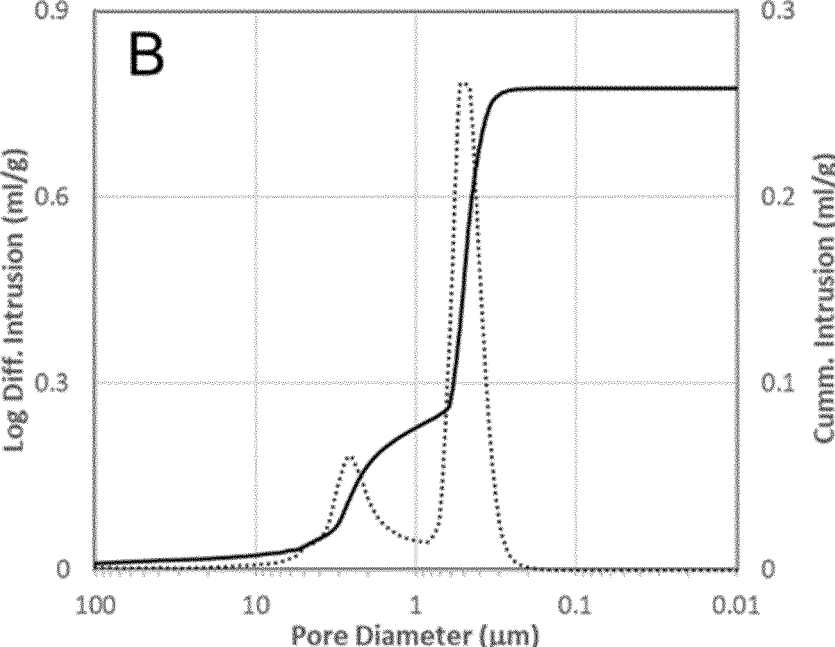
FIG. 2 shows the log differential intrusion [mL/g] and cumulative intrusion [mL/g] relative to the pore size diameter [mL/g] of inventive porous alpha-alumina catalyst support B, obtained by a process according to the invention.
Figure 3:
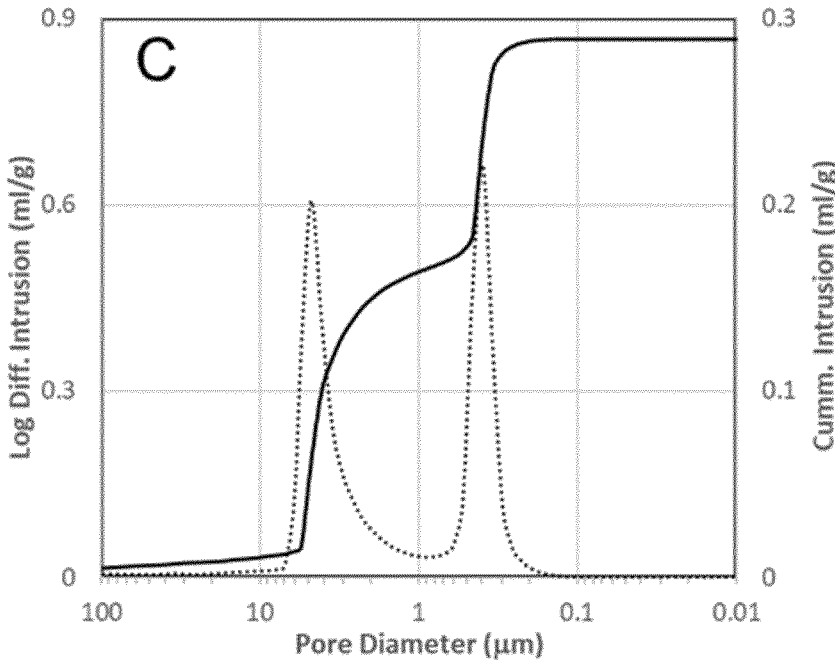
FIG. 3 shows the log differential intrusion [mL/g] and cumulative intrusion [mL/g] relative to the pore size diameter [mL/g] of comparative porous alpha-alumina catalyst support C.
Figure 4:
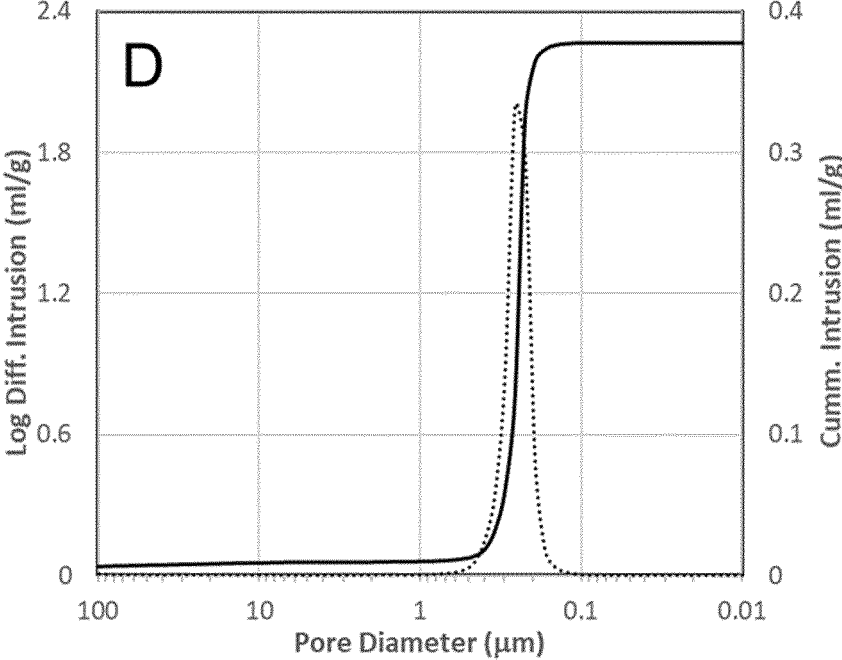
FIG. 4 shows the log differential intrusion [mL/g] and cumulative intrusion [mL/g] relative to the pore size diameter [mL/g] of inventive porous alpha-alumina catalyst support D, obtained by a process according to the invention.
Figure 5:
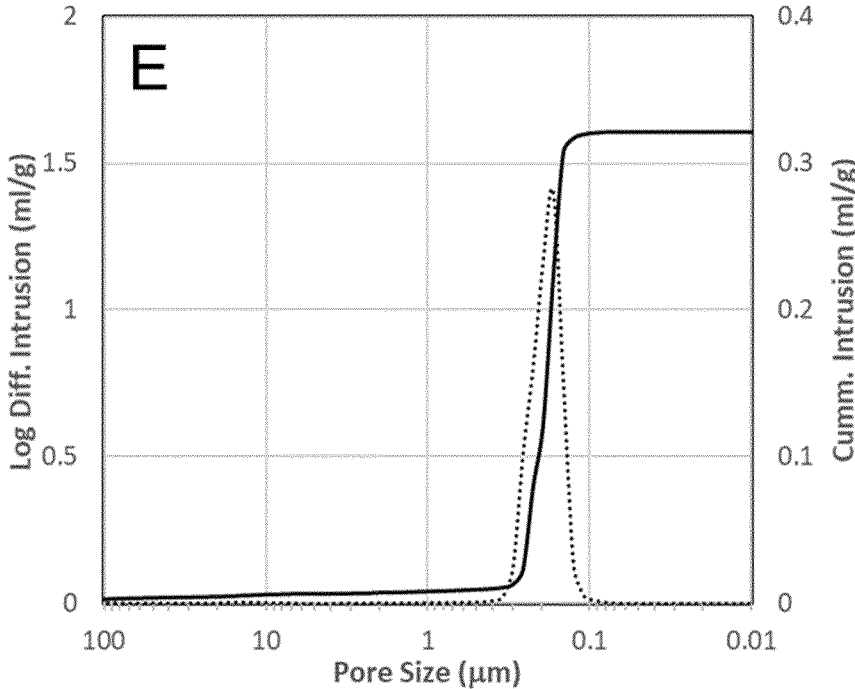
FIG. 5 shows the log differential intrusion [mL/g] and cumulative intrusion [mL/g] relative to the pore size diameter [mL/g] of inventive porous alpha-alumina catalyst support E, obtained by a process according to the invention.
Figure 6:
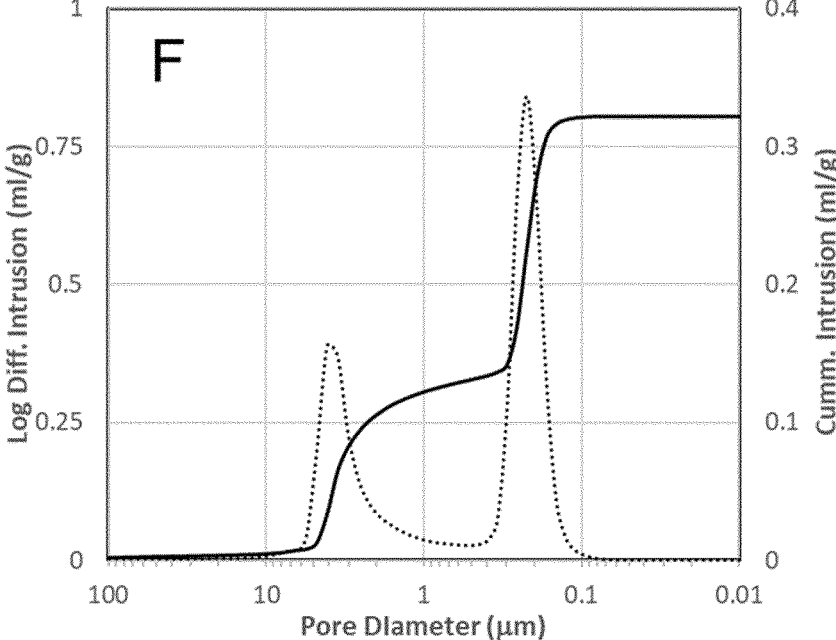
FIG. 6 shows the log differential intrusion [mL/g] and cumulative intrusion [mL/g] relative to the pore size diameter [mL/g] of comparative porous alpha-alumina catalyst support F.

Nitrogen sorption measurements were performed using a Micrometrics ASAP 2420. Nitrogen porosity was determined in accordance with DIN 66134. The sample was degassed at 200° C. for 16 h under vacuum prior to the measurement.

Method 2: Mercury Porosimetry

Mercury porosimetry was performed using a Micrometrics AutoPore V 9600 mercury porosimeter (140 degrees contact angle, 485 dynes/cm Hg surface tension, 61,000 psia max head pressure). Mercury porosity was determined in accordance with DIN 66133.

Samples were dried at 110° C. for 2 h and degassed under vacuum prior to analysis to remove any physically adsorbed species, such as moisture, from the sample surface.

Method 3: Loose Bulk Density

The loose bulk density was determined by pouring the transition alumina or alumina hydrate into a graduated cylinder via a funnel, taking care not to move or vibrate the graduated cylinder. The volume and weight of the transition alumina or alumina hydrate were determined. The loose bulk density was determined by dividing the volume in milliliters by the weight in grams.

Method 4: Bet Surface Area

The BET surface area was determined in accordance with DIN ISO 9277 using nitrogen physisorption conducted at 77 K. The surface area was obtained from a 5-point-BET plot. The sample was degassed at 200° C. for 16 h under vacuum prior to the measurement.

In the case of shaped alpha-alumina supports, more than 4 g of the sample were applied due to its relatively low BET surface area.

Method 5: Scanning Electron Microscopy

Scanning electron microscopy was performed using a Hitachi SU3500 VP SEM (12 nm Pt coating).

Method 6: Analysis of the Total Amount of Ca-, Mg-, Si-, Fe-, K-, and Na-Contents in Alpha-Alumina Supports 6A. Sample Preparation for Measurement of Ca, Mg, Si and Fe About 100 to 200 mg (at an error margin of ±0.1 mg) of a carrier sample were weighed into a platinum crucible. 1.0 g of lithium metaborate ($LiBO_2$) was added. The mixture was melted in an automated fusion apparatus with a temperature ramp up to max. 1150° C.

After cooling down, the melt was dissolved in deionized water by careful heating. Subsequently, 10 mL of semi-concentrated hydrochloric acid (concentrated HCl diluted with deionized water, volume ratio 1:1, corresponds to about 6 M) was added. Finally, the solution was filled up to a volume of 100 mL with deionized water.

6B. Measurement of Ca, Mg, Si and Fe

The amounts of Ca, Mg, Si and Fe were determined from the solution described under item 5A by Inductively Coupled Plasma—Optical Emission Spectroscopy (ICP-OES) using an ICP-OES Varian Vista Pro.

Parameters:

Wavelengths [nm]: Ca 317.933

Mg 285.213

Si 251.611

Fe 238.204

Integration time: 10 s

Nebulizer: Conikal 3 ml

Nebulizer pressure: 270 kPa

Pump rate: 30 rpm

Calibration: external (matrix-matched standards)

6C. Sample Preparation for Measurement of K and Na

About 100 to 200 mg (at an error margin of ±0.1 mg) of a carrier sample were weighed into a platinum dish. 10 mL of a mixture of aqueous concentrated $H_2SO_4$ (95 to 98%) and deionized water (volume ratio 1:4), and 10 mL of aqueous hydrofluoric acid (40%) were added. The platinum dish was placed on a sand bath and boiled down to dryness. After cooling down the platinum dish, the residue was dissolved in deionized water by careful heating. Subsequently, 5 mL of semi-concentrated hydrochloric acid (concentrated HCl diluted with deionized water, volume ratio 1:1, corresponds to about 6 M) were added. Finally, the solution was filled up to a volume of 50 mL with deionized water.

6D. Measurement of K and Na

The amounts of K and Na were determined from the solution described under item 5C by Flame Atomic Absorption Spectroscopy (F-AAS) using an F-AAS Shimadzu AA-7000.

Parameters:

Wavelengths [nm]: K 766.5 Na 589.0

Gas: Air/acetylene

Slit width: 0.7 nm (K)/0.2 nm (Na)

Nebulizer pressure: 270 kPa

Calibration: external (matrix-matched standards)

Preparation of Porous alpha-Alumina Catalyst Supports

The properties of the alumina raw materials used to obtain porous alpha-alumina catalyst supports are shown in Table 1. The transition aluminas and alumina hydrates were obtained from Sasol (Puralox®, and Pural®) and UOP (Versal®). alpha-Alumina was prepared by heating Puralox TH 200/70 at 1200° C. for 4 h.

TABLE 1

| | Bulk Density [g/L] | Pore Volume [mL/g] | Median Pore Diameter [nm] |
|---|---|---|---|
| alpha-Alumina | | | |
| Puralox TH 200/70, heated at 1200° C. | 556 | 0.60 ** | 58.8 ** |
| Transition Aluminas *** | | | |
| Puralox SCFa 140 | 650 | 0.57 * | 10.0 * |
| Puralox 200/90 | 460 | 0.68 * | 37.4 * |
| Puralox 400/50 | 390 | 0.90 ** | 112.4 ** |
| Puralox TM 100/150 | 420 | 0.87 * | 21.0 * |
| Puralox TM 100/150UF | 150 | 0.88 * | 18.4 * |
| Puralox TH 200/70 | 300 | 1.23 * | 37.4 * |
| Puralox TH 300/100 | 250 | 1.36 ** | 57.0 ** |
| Puralox TH 500/80 | 240 | 1.27 ** | 80.6 ** |
| Versal VGL-15 | 310 | 0.86 * | 21.7 * |
| Alumina Hydrates *** | | | |
| Pural SB1 | 680 | 0.55 * | 8.4 * |
| Pural 200 | 560 | 0.66 * | 35.6 * |
| Pural 400 | 450 | 0.93 ** | 107.4 ** |
| Pural TH 200 | 340 | 1.20 * | 37.6 * |

TABLE 1-continued

| | Bulk Density [g/L] | Pore Volume [mL/g] | Median Pore Diameter [nm] |
|---|---|---|---|
| Pural TH 300 | 260 | 1.30 ** | 57.0 ** |
| Pural TH 500 | 300 | 1.19 ** | 84.6 ** |
| Versal V-250 | 360 | 0.79 * | 9.9 * |

* determined by nitrogen sorption
** determined by mercury porosimetry
*** Puralox products are transition aluminas derived from Pural products, i.e. boehmite; Versal VGL-15 is a gamma-alumina derived from Versal V-250, i.e. pseudoboehmite

Example 1—Preparation of Supports A, B, C and G

Alumina raw materials, as specified in Table 1, were mixed to obtain a powder mixture. Kollidon® VA64 (a vinylpyrrolidone-vinyl acetate copolymer from BASF) was added to the powder mixture. Water was then added to obtain a malleable precursor material. The amounts of all components are shown in Table 2.

The malleable precursor material was mixed to homogeneity via a mix-muller and subsequently extruded using a ram extruder to form shaped bodies. The shaped bodies were in the form of hollow cylinders having an outer diameter of about 10 mm and an inner diameter of about 5 mm. The extrudates were dried at 110° C. for approximately 16 h, followed by heat treatment in a muffle furnace at 600° C. for 2 h with 5° C./min of ramping speed and subsequently at 1,500° C. for 2 h with 2° C./min of ramping speed. Heat treatment was performed in an atmosphere of air.

Example 2—Preparation of Supports D, E, F, H, I, J and K

Alumina raw materials, as specified in Table 1, were mixed to obtain a powder mixture. Colloidal silica (Ludox® AS 40, Grace & Co.) and petroleum jelly (Vaseline®, Unilever) were added to the powder mixture. Water was then added to obtain a malleable precursor material. The amounts of all components are shown in Table 2.

The malleable precursor material was mixed to homogeneity via a mix-muller and subsequently extruded using a ram extruder to form shaped bodies. The shaped bodies were in the form of hollow cylinders having an outer diameter of about 10 mm and an inner diameter of about 5 mm. The extrudates were dried at 110° C. for approximately 16 h, followed by heat treatment in a muffle furnace at 600° C. for 2 h with 5° C./min of ramping speed and subsequently at 1,425° C. for 4 h with 2° C./min of ramping speed. Heat treatment was performed in an atmosphere of air.

Example 3—Preparation of Supports L, M, N, O, P, Q and R

Alumina raw materials, as specified in Table 1, were mixed to obtain a powder mixture. Dispersible boehmite (Disperal® HP 14/7, Sasol) pre-dispersed in water and petroleum jelly (Vaseline®, Unilever) were added to the powder mixture. Water was then added to obtain a malleable precursor material. The amounts of all components are shown in Table 2.

The malleable precursor material was mixed to homogeneity via a mix-muller and subsequently extruded using a ram extruder to form shaped bodies. The shaped bodies were in the form of hollow cylinders having an outer diameter of about 10 mm and an inner diameter of about 5 mm. The extrudates were dried at 110° C. for approximately 16 h, followed by heat treatment in a muffle furnace at 600° C. for 2 h with 5° C./min of ramping speed and subsequently at 1,425° C. for 4 h with 2° C./min of ramping speed. Heat treatment was performed in an atmosphere of air.

TABLE 2

| Support | Transition Alumina | Alumina Hydrate | Binder | Processing Aid | Liquid |
|---|---|---|---|---|---|
| A | Puralox TH 200/70 340 g | Pural SB1 146 g | Kollidon VA64 15 g | — | Water 454 g |
| B | Puralox TM 100/150 340 g | Pural SB1 146 g | Kollidon VA64 15 g | — | Water 439 g |
| C * | Puralox SCFa 140 340 g | Pural SB1 146 g | Kollidon VA64 15 g | — | Water 379 g |
| G * | Puralox TH 200/70 Calcined at 1200° C. 271 g | Pural SB1 117 g | Kollidon VA64 12 g | — | Water 233 g |
| D | Puralox TH 200/70 320 g Puralox TM 100/150 UF 138 g | Pural TH 200 17 g | Silica Sol 1.5 g | Petroleum Jelly 23.6 g | Water 411 g |
| E | Puralox 200/90 256 g Puralox TM 100/150 UF 110 g | Pural 200 13 g | Silica Sol 1.2 g | Petroleum Jelly 19.0 g | Water 253 g |
| H | Puralox 400/50 256 g Puralox TM 100/150 UF 110 g | Pural 400 14 g | Silica Sol 1.2 g | Petroleum Jelly 19.1 g | Water 234 g |
| I | Puralox TH 300/100 256 g Puralox TM 100/150 UF 110 g | Pural TH 300 13 g | Silica Sol 1.2 g | Petroleum Jelly 19.1 g | Water 333 g |
| J | Puralox TH 500/80 256 g Puralox TM 100/150 UF 110 g | Pural TH 500 13 g | Silica Sol 1.2 g | Petroleum Jelly 19.0 g | Water 300 g |
| K | Versal VGL-15 256 g Puralox TM 100/150 UF 110 g | Versal V-250 13 g | Silica Sol 1.2 g | Petroleum Jelly 19.0 g | Water 335 g |
| F * | Puralox SCFa 140 320 g Puralox TM 100/150 UF 138 g | Pural SB1 17 g | Silica Sol 1.5 g | Petroleum Jelly 23.3 g | Water 347 g |
| L | Puralox TH 200/70 198 g Puralox TM 100/150 UF 108 g | Pural TH 200 74 g | Dispersible Boehmite 1.8 g | Petroleum Jelly 18.6 g | Water 310 g |
| M | Puralox TH 200/70 198 g Puralox TM 100/150 UF 108 g | Pural TM 100 74 g | Dispersible Boehmite 1.8 g | Petroleum Jelly 18.6 g | Water 315 g |
| N | Puralox TH 300/100 198 g Puralox TM 100/150 UF 107 g | Pural TH 300 74 g | Dispersible Boehmite 1.9 g | Petroleum Jelly 19.1 g | Water 272 g |
| O | Puralox 200/90 198 g Puralox TM 100/150 UF 107 g | Pural 200 74 g | Dispersible Boehmite 1.9 g | Petroleum Jelly 19.0 g | Water 233 g |
| P | Versal VGL-15 198 g Puralox TM 100/150 UF 107 g | Versal V-250 74 g | Dispersible Boehmite 1.9 g | Petroleum Jelly 19.0 g | Water 335 g |
| Q * | Puralox SCFa 140 198 g Puralox TM 100/150 UF 107 g | Pural SB1 74 g | Dispersible Boehmite 1.8 g | Petroleum Jelly 18.5 g | Water 291 g |
| R * | Puralox TH 200/70 Calcined at 1200° C 198 g Puralox TM 100/150 UF 107 g | Pural TH 200 74 g | Dispersible Boehmite 1.9 g | Petroleum Jelly 19.0 g | Water 219 g |

* comparative example

Table 3 shows the physical properties of all the supports prepared as shown in table 2. FIGS. 1 to 16 show the log differential intrusion and cumulative intrusion relative to the pore size diameter of all the supports prepared as shown in table 2.

TABLE 3

| Support | BET Surface Area [m²/g] | Pore Volume [mL/g] ** | Pore Volume Contained in Pores [mL/g] ** (Proportion of the Total Pore Volume) | | | | | $r_{pv}$ *** |
|---|---|---|---|---|---|---|---|---|
| | | | <0.1 μm | 0.1-1 μm | 1-10 μm | 10-100 μm | >100 μm | |
| A | 1.57 | 0.27 | 0 (0%) | 0.21 (77.9%) | 0.05 (16.9%) | 0.01 (5.2%) | 0 (0%) | 0.23 |
| B | 1.65 | 0.26 | 0 (0%) | 0.18 (71.0%) | 0.07 (25.9%) | 0.01% (3.1%) | 0 (0%) | 0.39 |
| C * | 1.30 | 0.29 | 0 (0%) | 0.12 (42.9%) | 0.16 (53.6%) | 0.01 (3.5%) | 0 (0%) | 1.33 |
| G * | 0.37 | 0.06 | 0 (0%) | 0.05 (83.3%) | 0.01 (17.7%) | 0 (0%) | 0 (0%) | 0.2 |
| D | 4.76 | 0.38 | 0 (0%) | 0.37 (97.4%) | 0.00 (0.0%) | 0.01 (2.6%) | 0 (0%) | 0.00 |
| E | 5.69 | 0.32 | 0 (0%) | 0.31 (96.9%) | 0.00 (0.0%) | 0.01 (3.1%) | 0 (0%) | 0.00 |
| H | 5.15 | 0.33 | 0 (0%) | 0.33 (100%) | 0 (0%) | 0 (0%) | 0 (0%) | 0.00 |
| I | 5.79 | 0.40 | 0 (0%) | 0.40 (100%) | 0 (0%) | 0 (0%) | 0 (0%) | 0.00 |
| J | 5.61 | 0.40 | 0 (0%) | 0.39 (97.5%) | 0.01 (2.5%) | 0 (0%) | 0 (0%) | 0.03 |
| K | 5.79 | 0.38 | 0 (0%) | 0.38 (100%) | 0 (0%) | 0 (0%) | 0 (0%) | 0.00 |
| F * | 3.20 | 0.32 | 0 (0%) | 0.20 (62.5%) | 0.12 (37.5%) | 0.00 (0.0%) | 0 (0%) | 0.60 |
| L | 2.77 | 0.32 | 0 (0%) | 0.32 (100%) | 0 (0%) | 0 (0%) | 0 (0%) | 0.00 |
| M | 2.64 | 0.34 | 0 (0%) | 0.32 (94.1%) | 0.01 (2.9%) | 0.01 (2.9%) | 0 (0%) | 0.03 |
| N | 2.60 | 0.29 | 0 (0%) | 0.29 (100%) | 0 (0%) | 0 (0%) | 0 (0%) | 0.00 |

TABLE 3-continued

| Support | BET Surface Area [m²/g] | Pore Volume [mL/g] ** | Pore Volume Contained in Pores [mL/g] ** (Proportion of the Total Pore Volume) | | | | | $r_{pv}$ *** |
|---|---|---|---|---|---|---|---|---|
| | | | <0.1 μm | 0.1-1 μm | 1-10 μm | 10-100 μm | >100 μm | |
| O | 2.50 | 0.27 | 0 (0%) | 0.26 (96.3%) | 0.01 (3.7%) | 0 (0%) | 0 (0%) | 0.04 |
| P | 2.97 | 0.33 | 0 (0%) | 0.33 (100%) | 0 (0%) | 0 (0%) | 0 (0%) | 0.00 |
| Q * | 2.16 | 0.28 | 0 (0%) | 0.17 (60.7%) | 0.10 (35.7%) | 0.01 (3.6%) | 0 (0%) | 0.59 |
| R * | 0.79 | 0.12 | 0 (0%) | 0.10 (83.3%) | 0.02 (17.7%) | 0 (0%) | 0 (0%) | 0.2 |

* comparative example
** determined by mercury porosimetry
*** $r_{pv}$ = ratio of the pore volume contained in pores with a diameter in the range of more than 1 to 10 μm to the pore volume contained in pores with a diameter in the range of 0.1 to 1 μm It is evident that the inventive supports exhibit advantageously high proportions of pores with a diameter in the range of 0.1 to 1 μm in comparison to the comparative supports C, F and Q. The inventive supports also exhibit lower $r_{pv}$ values than the comparative supports C, F and Q. The surface areas of the inventive supports are significantly larger than that of the comparative supports C, F and Q.

Compared to the comparative supports G and R, which are derived from alpha-alumina, the inventive supports exhibit significantly larger total pore volume and BET surface area.

Figure 7:
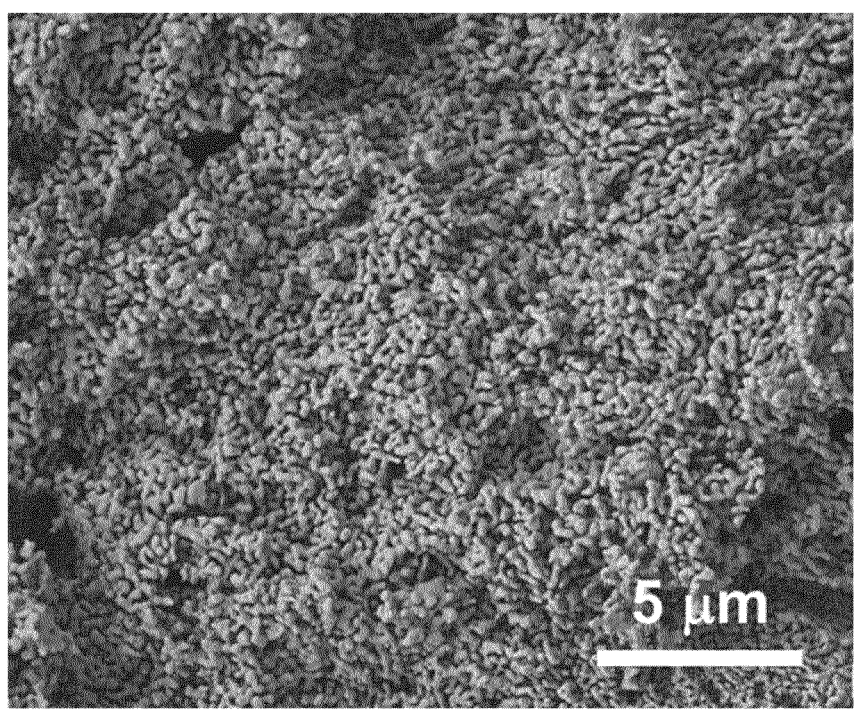
FIG. 7 shows an image of inventive porous alpha-alumina catalyst support D, as obtained by scanning electron microscopy.
Figure 8:
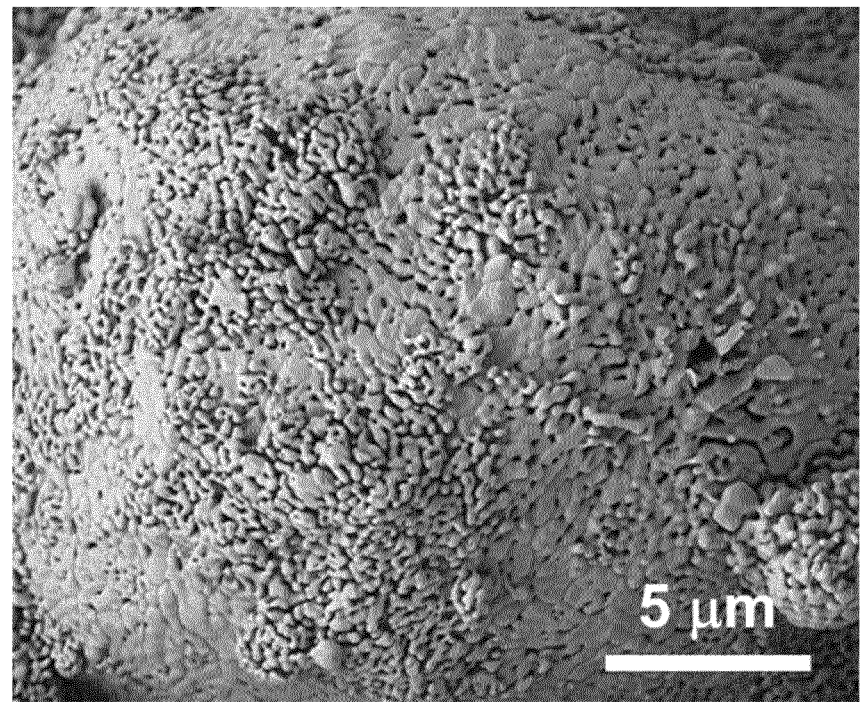
FIG. 8 shows an image of comparative porous alpha-alumina catalyst support F, as obtained by scanning electron microscopy.

Concurrently, the inventive supports exhibit a more open pore structure in comparison to the comparative supports, as is evident from the comparison of FIG. 7 (inventive support D) and FIG. 8 (comparative support F).

Example 4—Preparation of Supports S and T for Catalyst Performance Test

Transition aluminas and alumina hydrates, as specified in Table 1, were mixed to obtain a powder mixture. Processing aids (Vaseline®, Unilever and Glycerin, Sigma-Aldrich) and water were added to the powder mixture. Vivapur® MCC Spheres 200 (Microcrystalline Cellulose, JRS Pharma) was added to the mixture. Additional water was then added to obtain a malleable precursor material. The total amounts of all components are shown in Table 4.

TABLE 4

| Support | Transition Alumina | Alumina Hydrate | Pore Former | Processing Aid | Liquid |
|---|---|---|---|---|---|
| S | Puralox TH 200/70 173 g Puralox TM 100/150 UF 93 g | Pural TH 200 67 g | Vivapur MCC Spheres 200 250 g | Vaseline 8.5 g Glycerin 8.4 g | Water 454 g |
| T * | Puralox SCFa 140 173 g Puralox TM 100/150 UF 93 g | Pural SB1 67 g | Vivapur MCC Spheres 200 250 g | Vaseline 8.3 g Glycerin 8.3 g | Water 479 g |

* comparative example

Figure 9:
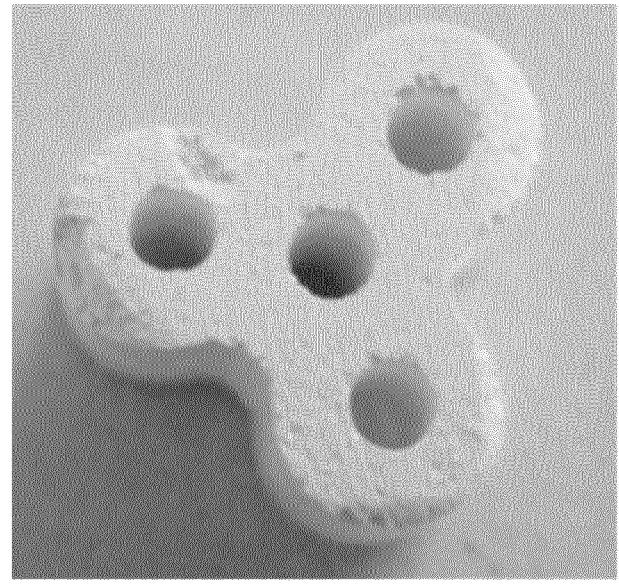
FIG. 9 shows the shape of the porous alpha-alumina catalyst supports S and T.
Figure 9:
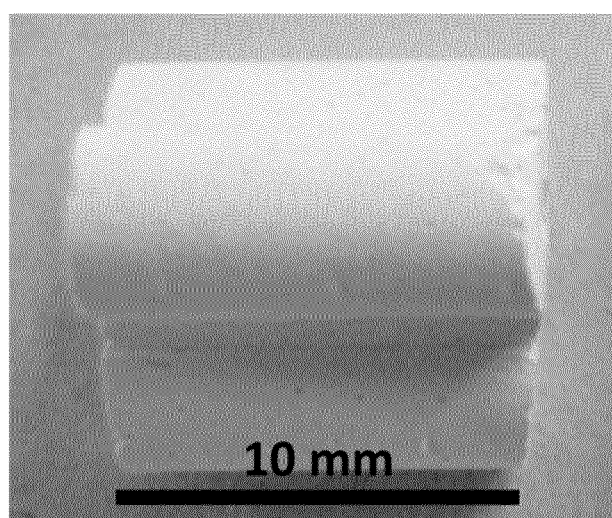

The malleable precursor material was mixed to homogeneity via a mix-muller and subsequently extruded using a ram extruder to form shaped bodies. The shaped bodies were in the form of a trilobe with 4 passageways, as depicted in FIG. 9. The extrudates were dried at 110° C. overnight (for approximately 16 h), followed by heat treatment in a muffle furnace at 600° C. for 2 h with 5° C./min of ramping speed and subsequently at high temperature (1475° C. for support S, 1430° C. for support T) for 4 h with 2° C./min of ramping speed. Heat treatment was performed in an atmosphere of air.

The dimensions of the dried supports were determined using a caliper. The diameter of the circumscribed circle of the cross-section perpendicular to the support height was 11.6 cm. The term "circumscribed circle" refers to the smallest circle that completely contains the trilobed cross-section within it. The diameter of the inscribed circle of the cross-section perpendicular to the support height was 5.3 cm. The term "inscribed circle" refers to the largest possible circle that can be drawn inside the trilobed cross-section. The central passageway had a diameter of 1.92 cm. The three outer passageways had a diameter of 1.46 cm.

The resulting supports S and T had an alpha-alumina content of more than 98 wt.-% and Na-, K-, Mg-, Ca-contents below 100 ppm. The Fe-content in both supports was 200 ppm. The Si-content in support S was 100 ppm. The Si-content in support T was 200 ppm.

Table 5 shows the physical properties of inventive support S and comparative support T.

TABLE 5

| | BET Surface Area | Pore Volume | Pore Volume Contained in Pores [mL/g] ** (Proportion of the Total Pore Volume) | | | | | |
|---|---|---|---|---|---|---|---|---|
| Support | [m²/g] | [mL/g] ** | <0.1 μm | 0.1-1 μm | 1-10 μm | 10-100 μm | >100 μm | $r_{pv}$ *** |
| S | 2.00 | 0.57 | 0 (0%) | 0.40 (70.2%) | 0.12 (21.1%) | 0.04 (7.0%) | 0.01 (1.8%) | 0.30 |
| T * | 1.95 | 0.53 | 0 (0%) | 0.22 (41.5%) | 0.21 (39.6%) | 0.09% (17.0%) | 0.01 (1.9%) | 0.95 |

* comparative example
** determined by mercury porosimetry
*** $r_{pv}$ = ratio of the pore volume contained in pores with a diameter in the range of more than 1 to 10 μm to the pore volume contained in pores with a diameter in the range of 0.1 to 1 μm

Example 5—Preparation of Catalysts

Shaped catalyst bodies were prepared by impregnating supports S and T with a silver impregnation solution. The catalyst compositions are shown in Table 6 below. Silver contents are provided in percent, relative to the total weight of the catalyst. Dopant values are provided in parts per million, relative to the total weight of the catalyst.

TABLE 6

Catalyst composition (Ag-contents are reported in percent by weight of total catalyst, dopant values are reported in parts per million by weight of total catalyst)

| Catalyst | Support | $Ag_{CAT}$ ** [wt-%] | $Li_{CAT}$ [ppm] | $S_{CAT}$ [ppm] | $W_{CAT}$ [ppm] | $Cs_{CAT}$ [ppm] | $Re_{CAT}$ [ppm] | $K_{ADD}$ *** [ppm] |
|---|---|---|---|---|---|---|---|---|
| 1 | S | 27.7 | 450 | 35 | 615 | 1025 | 1270 | 85 |
| 2 * | T * | 27.7 | 450 | 35 | 615 | 1025 | 1270 | 85 |

* comparative example

** Ag and all promoter values are calculated values;

*** $K_{ADD}$ is understood to mean the amount of potassium added during impregnation and does not include the amount of potassium comprised in the alumina support prior to impregnation.

5.1 Production of a Silver Complex Solution

A silver complex solution was prepared according to Production Example 1 of WO 2019/154863 A1. The silver complex solution had a density of 1.529 g/mL, a silver content of 29.3 wt.-% and a potassium content of 90 ppm.

5.2. Preparation of Intermediate Catalysts 100.0 g of support S (intermediate 1.1) or 100.4 g of support T (intermediate 1.2) were each placed into a 2 L glass flask. The flask was attached to a rotary evaporator, which was set under a vacuum pressure of 80 mbar. The rotary evaporator system was set in rotation of 30 rpm. 76.55 g (intermediate 1.1) or 76.86 g (intermediate 1.2) of silver complex solution prepared according to step 2.1 were added onto support S (intermediate 1.1) or support T (intermediate 1.2) over 15 min under a vacuum pressure of 80 mbar. After addition of the silver complex solution, the rotary evaporator system was continued to rotate under vacuum for a further 15 min. The impregnated support was then left in the apparatus at room temperature (approximately 25° C.) and atmospheric pressure for 1 h and mixed gently every 15 min.

The impregnated material was placed on a net forming 1 to 2 layers. The net was subjected to 23 Nm³/h of air flow, wherein the gas flow was pre-heated to a temperature of 305° C. The impregnated material was heated up to a temperature of 290° C. at a heating rate of about 30 K/min and then maintained at 290° C. for 8 min to yield Ag-containing intermediate products according to Table 7. The temperatures were measured by placing three thermocouples at 1 mm below the net. Subsequently, the catalysts were cooled to ambient temperature by removing the intermediate catalyst bodies from the net using an industrial vacuum cleaner.

TABLE 7

Ag containing intermediate catalysts (Ag-contents are reported in percent by weight of total catalyst, dopant values are reported in parts per million by weight of total intermediate catalyst)

| Intermediate | Support | $Ag_{CAT}$ ** [wt.-%] | $K_{ADD}$ *** [ppm] |
|---|---|---|---|
| 1.1 | S | 18.3 | 56 |
| 1.2 | T * | 18.3 | 56 |

* comparative example

** Ag and all promoter values are calculated values;

*** $K_{ADD}$ is understood to mean the amount of potassium added during impregnation and does not include the amount of potassium comprised in the alumina support prior to impregnation;

5.3. Preparation of Catalysts 120.5 g of Ag-containing intermediate product 1.1 or 122.2 g of Ag-containing intermediate product 1.2 as prepared according to step 2.2 were each placed into a 2 L glass flask. The flask was attached to a rotary evaporator which was set under vacuum pressure of 80 mbar. The rotary evaporator system was set in rotation of 30 rpm. For the catalyst 1, 53.80 g of the silver complex solution prepared according to step 2.1 was mixed with 2.16 g of promoter solution I, 2.80 g of promoter solution II, and 4.69 g of promoter solution III. For the catalyst 2, 54.56 g of the silver complex solution prepared according to step 2.1 was mixed with 2.19 g of promoter solution I, 2.84 g of promoter solution II, and 4.76 g of promoter solution III.

Promoter solution I was obtained by dissolving lithium nitrate (Merck, 99.995%) and ammonium sulfate (Merck, 99.4%) in DI water to achieve a Li content of 2.85 wt.-% and a S content of 0.22 wt.-%. Promoter solution II was obtained by dissolving tungstic acid (HC Starck, 99.99%) in DI water and cesium hydroxide in water (HC Starck, 50.42%) to achieve a target Cs content of 5.0 wt.-% and a W content of 3.0 wt.-%. Promoter solution III was obtained by dissolving ammonium perrhenate (Buss & Buss Spezialmetalle GmbH, 99.9%) in DI water to achieve a Re content of 3.7 wt.-%.

The combined impregnation solution containing silver complex solution and promoter solutions I, II, and III was stirred for 5 minutes. The combined impregnation solution was added onto each of the silver-containing intermediate products 1.1 or 1.2 over 15 min under a vacuum pressure of 80 mbar. After addition of the combined impregnation solution, the rotary evaporator system was continued to rotate under vacuum for another 15 min. The impregnated support was then left in the apparatus at room temperature (about 25° C.) and atmospheric pressure for 1 h and mixed gently every 15 min.

The impregnated material was placed on a net forming 1 to 2 layers. The net was subjected either to 23 Nm³/h nitrogen flow (oxygen content: <20 ppm), wherein the gas flow was pre-heated to a temperature of 305° C. The impregnated materials were heated up to a temperature of 290° C. at a heating rate of about 30 K/min and then maintained at 290° C. for 7 min to yield catalysts according to Table 4. The temperatures were measured by placing three thermocouples at 1 mm below the net. Subsequently, the catalysts were cooled to ambient temperature by removing the catalyst bodies from the net using an industrial vacuum cleaner.

Example 6—Catalyst Testing

An epoxidation reaction was conducted in a vertically-placed test reactor constructed from stainless steel with an inner diameter of 6 mm and a length of 2.2 m. The reactor was heated using hot oil contained in a heating mantel at a specified temperature. All temperatures below refer to the temperature of the hot oil. The reactor was filled with 9 g of inert steatite balls (0.8 to 1.1 mm), onto which 26.4 g of crushed catalyst screened to a desired particle size of 1.0 to 1.6 mm were packed, and thereon an additional 29 g of inert steatite balls (0.8-1.1 mm) were packed. The inlet gas was introduced to the top of the reactor in a "once-through" operation mode.

The catalysts were charged into the reactor at a reactor temperature of 90° C. under nitrogen flow of 130 N L/h at a pressure of 1.5 bar absolute. Then, the reactor temperature was ramped up to 210° C. at a heating rate of 50 K/h and the catalysts were maintained at this condition for 15 h. Then, the nitrogen flow was substituted by a flow of 114 N L/h methane and 1.5 NL/h $CO_2$. The reactor was pressurized to 16 bar absolute. Then 30.4 NL/h ethylene and 0.8 NL/h of a mixture of 500 ppm ethylene chloride in methane were added. Then, oxygen was introduced stepwise to reach a final flow of 6.1 NL/h. At this point the inlet composition consisted of 20 vol.-% ethylene, 4 vol.-% oxygen, 1 vol.-% carbon dioxide, and ethylene chloride (EC) moderation of 2.5 parts per million by volume (ppmv), with methane used as a balance at the total gas flow rate of 152.8 NL/h. The reactor temperature was ramped up to 225° C. at a heating rate of 5 K/h and afterwards to 240° C. at a heating rate of 2.5 K/h. The catalysts were maintained at this condition for 135 hours. Afterwards, EC concentration was decreased to 2.2 ppmv, and the temperature was decreased to 225° C. Then, the inlet gas composition was gradually changed to 35 vol.-% ethylene, 7 vol.-% oxygen, 1 vol.-% carbon dioxide with methane used as a balance and a total gas flow rate of 147.9 NL/h. The temperature was adjusted to achieve an ethylene oxide (EO) concentration in the outlet gas of 3.05%. The EC concentration was adjusted to optimize the selectivity. Results of the catalyst tests are summarized in Table 8.

TABLE 8

Summary of Catalyst Tests

| Catalyst | Support | Time on stream** [h] | EO-Selectivity [%] | Reactor Temperature [° C.] |
|----------|---------|----------------------|--------------------|-----------------------------|
| 1 | S | 600 | 89.0 | 235 |
| 2 * | T * | 600 | 87.9 | 234 |

* comparative example
**Time on stream begins from the point of introduction of oxygen to the ethylene containing feed It is evident that catalyst 1 obtained from inventive support S shows much higher selectivity than catalyst 2 obtained from comparative support T.

The invention claimed is:

1. A process for producing a porous alpha-alumina catalyst support, comprising
   i) preparing a precursor material comprising, based on inorganic solids content,
      at least 50 wt.-% of a transition alumina having a loose bulk density of at most 600 g/L, a pore volume of at least 0.6 mL/g and a median pore diameter of at least 15 nm; and
      at most 30 wt.-% of an alumina hydrate;
   ii) forming the precursor material into shaped bodies; and
   iii) calcining the shaped bodies to obtain the porous alpha-alumina catalyst support.

2. The process according to claim 1, wherein the transition alumina has a loose bulk density in the range of 50 to 600 g/L and a pore volume of 0.6 to 2.0 mL/g.

3. The process according to claim 1, wherein the precursor material comprises 1 to 30 wt.-% of the alumina hydrate.

4. The process according to claim 1, wherein the transition alumina comprises a phase selected from gamma-alumina, delta-alumina and theta-alumina.

5. The process according to claim 1, wherein the transition alumina comprises at least 50 wt.-% of a transition alumina having an average particle size of 10 to 100 μm based on the total weight of transition alumina.

6. The process according to claim 1, wherein the alumina hydrate comprises boehmite and/or pseudoboehmite.

7. The process according to claim 1, wherein the precursor material further comprises a liquid.

8. The process according to claim 1, wherein the precursor material further comprises pore-forming materials, lubricants, organic binders, and/or inorganic binders.

9. The process according to claim 1, wherein the precursor material is formed into shaped bodies via extrusion, tableting, granulation casting, molding, or micro-extrusion.

10. The process according to claim 1, wherein calcining is performed at a temperature of at least 1300° C.

* * * * *